US012336887B2

(12) United States Patent
Rodzewicz et al.

(10) Patent No.: US 12,336,887 B2
(45) Date of Patent: Jun. 24, 2025

(54) MEDICAL DRESSING

(71) Applicant: Mölnlycke Health Care AB, Gothenburg (SE)

(72) Inventors: Patrick Rodzewicz, Gothenburg (SE); Jenny Flach, Alingsås (SE); Maria Gustin Bergström, Linköping (SE); Karin Östan, Nödinge (SE); Sandra Tillman, Gothenburg (SE); Angelica Andresen, Kungsbacka (SE); Anita Haraldsson Hedbratt, Mölnlycke (SE)

(73) Assignee: Mölnlycke Health Care AB, Mölndal (SE)

( * ) Notice: Subject to any disclaimer, the term of this patent is extended or adjusted under 35 U.S.C. 154(b) by 0 days.

(21) Appl. No.: 18/595,740

(22) Filed: Mar. 5, 2024

(65) Prior Publication Data

US 2024/0252360 A1 Aug. 1, 2024

Related U.S. Application Data

(63) Continuation of application No. 16/312,216, filed as application No. PCT/EP2017/064548 on Jun. 14, 2017, now Pat. No. 11,957,547.

(30) Foreign Application Priority Data

Jun. 23, 2016 (EP) .................................. 16176008

(51) Int. Cl.
*A61F 13/0203* (2024.01)
*A61F 13/00* (2024.01)
(Continued)

(52) U.S. Cl.
CPC ...... *A61F 13/022* (2013.01); *A61F 13/15203* (2013.01); *A61F 17/00* (2013.01);
(Continued)

(58) Field of Classification Search
CPC ...... A61F 13/02; A61F 13/00; A61F 13/0223; A61F 13/0226; A61F 13/0259;
(Continued)

(56) References Cited

U.S. PATENT DOCUMENTS 5,512,041 A * 4/1996 Bogart .................. A61F 13/023
602/56
5,540,922 A 7/1996 Fabo
(Continued)

FOREIGN PATENT DOCUMENTS

| EP | 2752176 A1 | 7/2014 |
| WO | 0239940 A2 | 5/2002 |
| WO | 2008149107 | 12/2008 |

OTHER PUBLICATIONS

"Covestro Platilon® U073 Polyurethane (Ether) Film", Available Online at: https://www.matweb.com/search/datasheettext.aspx?matguid=08da574575be47a1ac9ddfdc263c8f04, 2022, 2 pages.
(Continued)

*Primary Examiner* — Alireza Nia
*Assistant Examiner* — Gina McCarthy
(74) *Attorney, Agent, or Firm* — Ballard Spahr LLP

(57) ABSTRACT

A medical dressing is provided. The dressing has a central portion and a border portion, and comprises a backing layer, an adhesive body contact layer and a pad arranged in the central portion between the backing layer and the adhesive body contact layer. The pad is symmetric about a longitudinal center line and the dressing comprises a lobed portion on each side of the center line. The central portion of the dressing has a tensile strength in the longitudinal (y) direction of at least 60 N, preferably at least 70 N at an elongation of 25%, as measured by the test method ASTM D 882-12. The medical dressing may be used for pressure ulcer prevention, such as at the sacrum region of a human body.

21 Claims, 13 Drawing Sheets

(51) Int. Cl.
*A61F 13/15* (2006.01)
*A61F 17/00* (2006.01)

(52) U.S. Cl.
CPC .............. *A61F 2013/00272* (2013.01); *A61F 2013/00404* (2013.01); *A61F 2013/00829* (2013.01); *A61F 2013/15024* (2013.01); *A61F 2013/15284* (2013.01)

(58) Field of Classification Search
CPC .............. A61F 13/023; A61F 13/00085; A61F 13/0243; A61F 13/0246; A61F 13/022; A61F 13/00055; A61F 2013/00089; A61F 2013/00817; A61F 2013/00829; A61F 2013/5024; A61F 2013/15284; A61F 2013/5934; A61F 2013/53062; A61F 2013/53925; A61F 2013/00272; A61F 2013/00387; A61F 2013/00404; A61F 2013/00582; A61F 2013/00591; A61F 2013/00595; A61F 2013/00744; A61F 2013/00361; A61F 2013/006; A61F 2013/15024; A61F 13/0203; A61F 13/0213; A61F 13/53; A61F 13/534; A61F 13/476; A61F 13/15; A61F 13/15203; A61F 17/00; A61L 15/425; D04H 1/43828
See application file for complete search history.

(56) References Cited

U.S. PATENT DOCUMENTS

| | | | |
|---|---|---|---|
| 5,649,917 | A | 7/1997 | Roberts et al. |
| 5,704,905 | A * | 1/1998 | Jensen ............... A61F 13/0213 602/42 |
| 5,772,623 | A | 6/1998 | Conte |
| 6,103,369 | A | 8/2000 | Lucast et al. |
| 7,531,711 | B2 * | 5/2009 | Sigurjonsson ........ A61L 15/425 602/41 |
| 8,791,321 | B2 | 7/2014 | Love et al. |
| 9,791,321 | B2 | 10/2017 | Chattopadhyay et al. |
| 2003/0082966 | A1 | 5/2003 | Menday et al. |
| 2003/0120243 | A1 | 6/2003 | Uitenbroek et al. |
| 2006/0260974 | A1 | 11/2006 | Tucker |
| 2007/0224903 | A1 * | 9/2007 | Chakravarty ...... D04H 1/43828 442/361 |
| 2010/0204667 | A1 * | 8/2010 | Chakravarthy ..... A61F 13/0279 604/385.03 |
| 2011/0313383 | A1 | 12/2011 | Hofstetter et al. |
| 2012/0053545 | A1 * | 3/2012 | Love ........................ B32B 7/14 604/374 |
| 2016/0176165 | A1 * | 6/2016 | Liu ........................... C08L 1/00 428/354 |

OTHER PUBLICATIONS

U.S. Appl. No. 16/312,216 "Advisory Action", Oct. 18, 2021, 4 pages.
U.S. Appl. No. 16/312,216 "Corrected Notice of Allowability", Dec. 13, 2023, 3 pages.
U.S. Appl. No. 16/312,216 "Final Office Action", Jun. 22, 2023, 45 pages.
U.S. Appl. No. 16/312,216 "Final Office Action", Jun. 24, 2021, 35 pages.
U.S. Appl. No. 16/312,216 , "Final Office Action", May 27, 2022, 35 pages.
U.S. Appl. No. 16/312,216 , "Non-Final Office Action", Dec. 14, 2021, 28 pages.
U.S. Appl. No. 16/312,216 , "Non-Final Office Action", Jan. 22, 2021, 27 pages.
U.S. Appl. No. 16/312,216 , "Non-Final Office Action", Nov. 8, 2022, 39 pages.
U.S. Appl. No. 16/312,216 , "Notice of Allowance", Dec. 6, 2023, 16 pages.
PCT/EP2017/064548 , "International Search Report and Written Opinion", Jul. 10, 2017, 10 pages.

* cited by examiner

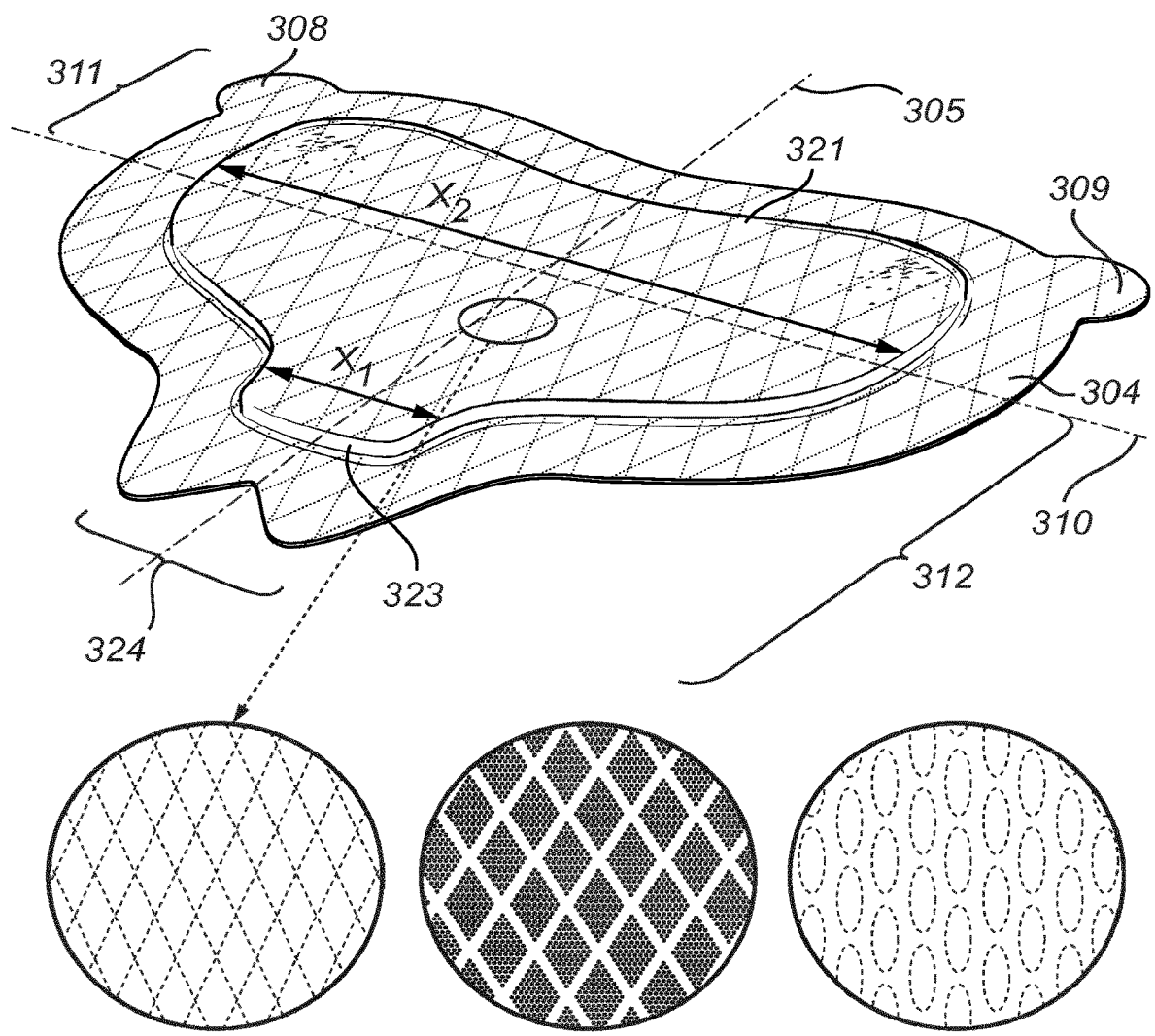
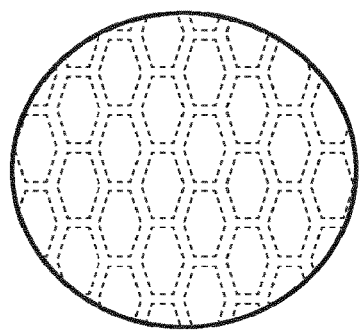
Fig. 5a  Fig. 5b  Fig. 5c
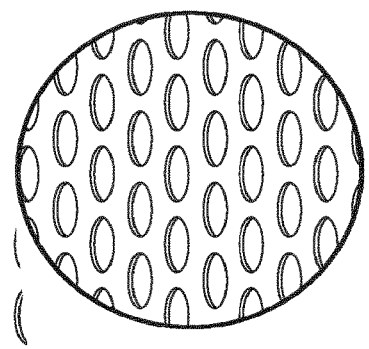
Fig. 5d  Fig. 5e

MEDICAL DRESSING

CROSS-REFERENCES TO RELATED APPLICATIONS

This application is a Continuation of application Ser. No. 16/312,216, filed Dec. 20, 2018, which is a National Stage of PCT Application No. PCT/EP2017/064548, filed Jun. 14, 2017, which claims the benefit of and the priority to EP Application No. 16176008.7, filed on Jun. 23, 2016, which are hereby incorporated by reference in their entireties for all purposes.

TECHNICAL FIELD

The present invention relates to a medical dressing comprising a backing layer, a pad and an adhesive body contact layer. The dressing is suitable for the prevention of pressure ulcers.

BACKGROUND ART

A pressure ulcer is a localized injury to the skin and/or the underlying tissue that results from pressure, typically in combination with friction and shear. Several factors can lead to pressure ulcers or pressure injuries, such as high pressure, uneven pressure distribution, disturbed microclimate, friction at the skin, and internal shear stresses. Pressure ulcers often arise among persons being bedridden for various reasons, such as for instance due to long term hospitalization or other causes of immobility. When the same location on the body is exposed to sustained pressure and shear, a pressure ulcer can develop in that location. Pressure ulcers typically develop in soft tissue under skin that covers bony areas of the body, for example the heels, ankles, the hips or the sacral buttocks. The necrosis in soft tissue spreads to the skin resulting in the formation of a pressure ulcer. Patients particularly at risk are those suffering from diabetes, cardiovascular conditions, incontinence, and arthritis.

The sacrum is an area that has a higher risk of developing pressure ulcers than other areas. The anatomy and physiology of the sacrum make the tissue very vulnerable to pressure. Patients that have been hospitalized or bedridden for a longer period of time require additional precautions to prevent sacrum ulceration. While pressure causes compression of the tissues, shear forces occur between the layers of the tissues and tend to tear and separate them. A pressure ulcer may originate in the soft tissue (fat or muscle) in the sacrum region, and spread to the skin, where it becomes visible.

Not only does a pressure ulcer cause great discomfort and/or pain to the affected person, but it also causes difficulties to nursing personnel and other care-takers. In addition, pressure ulcers represent a big challenge to the healthcare system and are associated with high costs.

Due to the effects on quality of life and strain on the healthcare system associated with pressure ulcers, it is desirable to act proactively, rather than reactively. In other words, instead of waiting for pressure ulcers to develop and then perform treatment, it is preferred to try to prevent the pressure ulcers from occurring in the first place.

Pressure ulcers are largely preventable. When pressure ulcers occur, they can become painful wounds that require months to heal. The prevention of pressure ulcers includes inspection of the skin, control of risk factors, keeping the skin clean and dry, and redistributing pressure over high risk bony areas.

To date, such preventative means typically include pressure off-loading or re-positioning the patient at regular intervals such that pressure is relieved or re-distributed, and the amount of pressure that the individual is exposed to is minimized. This can be a difficult and time-consuming task for caregivers to keep track of and ensuring that patients are repositioned according to a specific turning schedule, especially when there are multiple patients at risk for developing pressure ulcers.

Also, these methods are typically performed at a stage when a pressure ulcer has already developed, and serve to prevent the pressure sore formed from causing more harm to the patient. While many of the present approaches to deal with pressure ulcers are reactive, and serve to minimize the damage already made, there is a need in the art for a proactive approach in preventing pressure ulcers from even occurring in the first place. Such a method should be cost-efficient, simple and aid in relieving the burden for caregivers and staff in dealing with pressure ulcers.

SUMMARY OF THE INVENTION

It is an object of the present invention to fulfil the above mentioned need and to provide an efficient means to prevent the onset of pressure ulcers and to provide for beneficial technological and economical progress in the field of pressure ulcer prevention.

This object is achieved by providing a medical dressing for application to a contoured surface of a human body, the dressing having a central portion and a surrounding border portion and a lateral (x) and a longitudinal (y) extension; wherein the dressing comprises:
  a backing layer
  an adhesive body contact layer, and
  a pad arranged in the central portion between the backing layer and the body contact layer,
wherein the backing layer and the body contact layer extend beyond the periphery of the pad to define the border portion along the contour of the pad; the pad being symmetric about a longitudinal center line and the dressing comprising a first lobed portion on one side of the longitudinal center line and a second lobed portion on the other side of the longitudinal center line; wherein the central portion has a tensile strength in the longitudinal (y) direction of at least 60 N, preferably at least 70 N at an elongation of 25%, as measured by the test method ASTM D 882-12, modified as described in the specification.

The present invention is based on the realization that a dressing being stiff in the longitudinal (y) direction is suitable for protecting the skin cells, and deeper tissue layer cells from shear and compression resulting from long term exposure to pressure and sustained load, thereby preventing the onset of pressure ulcers. The dressing of the present invention is suitable for application onto the sacrum region of a patient. The sacrum is particularly subject to pressure and prone to developing sores, especially when patients are being bedridden during longer periods. The longitudinal (y) extension of the dressing corresponds to the direction of which the patient, wearing such dressing, slides in bed. This direction of the dressing is subject to most friction and is exposed to high shear forces. When a patient slides in bed, the skin (which is often moist from e.g. sweat) rubs against the bed sheet.

Also, as the adjustable head of a bed is elevated, the skin cells and the underlying tissue cells become stressed and stretched. This may result in tissue deformation and rubbing of the epidermis.

The inventors have found that a dressing having a substantial stiffness in this direction is able to withstand pressure and shear forces by "locking" the skin such that it is protected from stretching. The dressing "absorbs" the shear forces inflicted by the patient movements and prevents the skin cells and the underlying tissue cells from becoming damaged.

In embodiments, the central portion of the dressing has a wet tensile strength in the longitudinal (y) direction of at least 50 N, preferably at least 65 N at an elongation of 25%, as measured by the test method ASTM D 882-12, modified as described in the specification.

In order to protect the skin cells and the underlying tissue cells from deformation and deterioration, it is important that the stiffness in the longitudinal (y) direction and the integrity of the dressing structure is maintained when the dressing becomes wet. A dressing that is applied in the sacral region may be subject to high amounts of liquid, for example due to the patient being warm and sweaty, but also from urine in the case of an incontinent patient.

In embodiments, the tensile strength of the central portion of the dressing is higher in the longitudinal (y) direction than the tensile strength in the lateral (x) direction. For example, the tensile strength in the longitudinal (y) direction may be at least 2.5 times higher, preferably at least 4 times higher than the tensile strength in the lateral (x) direction.

The dressing is advantageously more stretchable in the lateral (x) direction. A bedridden patient at risk of developing pressure ulcers must be turned and repositioned at regular intervals. It is therefore important that the dressing conforms to this lateral movement and stays on the skin. If the dressing is too stiff in this direction, turning the patient would inflict more forces to the tissue outside the dressing and the dressing would fall off easier.

The adhesive body contact layer of the dressing may cover at least 60% of the surface of the pad.

This way, a large proportion of the pad stays adhered to the skin, which not only improves the stay-on ability of the dressing, but also aids in "locking" the skin and preventing it from becoming stretched. Also, the friction between the dressing and the skin is reduced.

The border portion may have a tensile strength of between 3.5 and 10 N, preferably between 4 and 6 N at an elongation of 25%, as measured by ASTM D 882-12.

Inspection of the skin is an important part of the prevention regimen for pressure ulcers. The caregiver must regularly inspect the skin. Sometimes, after inspection, the dressing must be removed, but many times the dressing can be re-applied onto the skin. It is therefore important to have a border portion with optimized handling properties. For inspection and handling purposes, it is important that the border portion has sufficient rigidity, yet being flexible enough to conform to contoured surfaces.

The backing layer of the medical dressing suitably has a friction coefficient of between 0.4 and 1 when measured by the standard test method ASTM D 1894-14. The friction coefficient is preferably low such that the friction between the dressing and the bed sheet is reduced when a patient slides in bed. Reducing friction is an important aspect, since friction is the source of shear. The backing layer acts as a "sliding layer" and prevents the translation of friction into harmful shear forces. The pad may comprise a first layer and a second layer; the first layer being arranged between the backing layer and the second layer of the pad, wherein the first layer has a higher affinity for liquid than the second layer.

This construction is beneficial as moisture can quickly be transported away from the second layer (being in closest contact with the skin) to the first layer. Also, heat energy generated may be wicked away from the skin. Since heat increases the metabolism of the already stressed cells under pressure, this could otherwise add to the deterioration of skin cells.

In embodiments, the border portion is substantially heart shaped such that the first and second lobed portions form part of the lobed upper sides of a heart shape. Suitably, the first and second lobed portions are separated by a forked portion which replaces the pointed lower part of a heart shape.

The shape of the medical dressing is adapted to fit to the sacral region of a human body. The forked portion allows for an improved stay on ability in the gluteal cleft region. Proper seal in the gluteal cleft area is desirable, for example to seal off from body fluids as a result of incontinence.

In embodiments, the pad is divided by a lateral center line into an upper pad region with an upper lateral edge and a lower pad region with a lower lateral edge, wherein the width, x1, of the lower lateral edge of the pad is between 10-40% of the maximum width, x2, of the pad in the lateral (x) direction.

The pad is arranged to taper downwards, towards the lower region and has a more narrow width in the lower region of the dressing. This shape of the pad allows for proper protection of the coccyx, which is a bony prominence at risk for the development of pressure ulcers. It also conforms to the gluteal cleft region of a human body.

To facilitate inspection of the skin, the dressing may comprise at least one gripping tab, wherein the tab is coplanar with and projects outwardly from the border portion of one of the lobed portions.

The gripping tab guides the caregiver to lift the dressing, inspect the skin underneath the dressing, and to thereafter re-apply the dressing onto the skin (in case the skin looks ok).

Since the inspection of the skin typically takes place where the patient is lying on the side in the bed, it is beneficial to have at least two gripping tabs such that the caregiver can lift the dressing regardless of which side the patient lies.

Hence, in embodiments, the gripping tab is a first gripping tab, and the dressing further comprises a second gripping tab that is coplanar with and projects outwardly from the second lobed portion.

The dressing may be divided by a lateral center line into an upper region and a lower region, the gripping tab(s) being located in the upper region of the dressing. The dressing may thus be lifted and pulled down, such that the lower region of the dressing; i.e. the region that is attached to the gluteal cleft, stays attached to the skin during inspection. This gives extra stability of the dressing during inspection, and prevents the formation of wrinkles in the border portion of the dressing when re-applied to the skin.

The distance between the outer perimeters of the first and second gripping tabs, respectively, is larger than the largest extension of the remaining part of the dressing in the lateral direction.

In this position, the forces applied for opening up the dressing are distributed evenly over the border, and prevents the border portion to collapse or fold against itself during inspection.

In embodiments, the backing layer comprises a functional enhancement print, wherein the functional enhancement print is asymmetric in the lateral (x) and longitudinal (y) directions in a non-stretched state.

The printed backing layer visually communicates to the user the differences in functionality of the dressing. It also aids in guiding the user to select a dressing suitable for prevention purposes, and to distinguish it from a dressing specifically directed towards treatment of wounds.

For example, the functional enhancement print may be a continuous print selected from a lattice of ellipses, rectangles and lines intersecting as crosses.

In another aspect, the present invention relates to a dressing as described hereinbefore for use in the prevention of pressure ulcers.

In yet another aspect, the present invention relates to a kit comprising the dressing as defined hereinbefore and at least one dressing suitable for application onto the heel.

The heels and the sacrum are regions at risk for the development of pressure ulcers, especially for patients being hospitalized for longer periods. The dressing of the invention may be packaged together with one or more heel dressings and provided as a kit for prevention of pressure ulcers. The kit may reduce the burden or workload for caregivers and nursing personnel.

BRIEF DESCRIPTION OF THE DRAWINGS

The objectives and features of the invention will become more readily apparent from the following detailed description taken in conjunction with the accompanying drawings, in which:

FIG. 1b is a cut out portion of the dressing in FIG. 1a.

FIGS. 5a-e illustrate a medical dressing according to at least one exemplary embodiment, comprising a functional enhancement print.

DETAILED DESCRIPTION

Figure 1A:
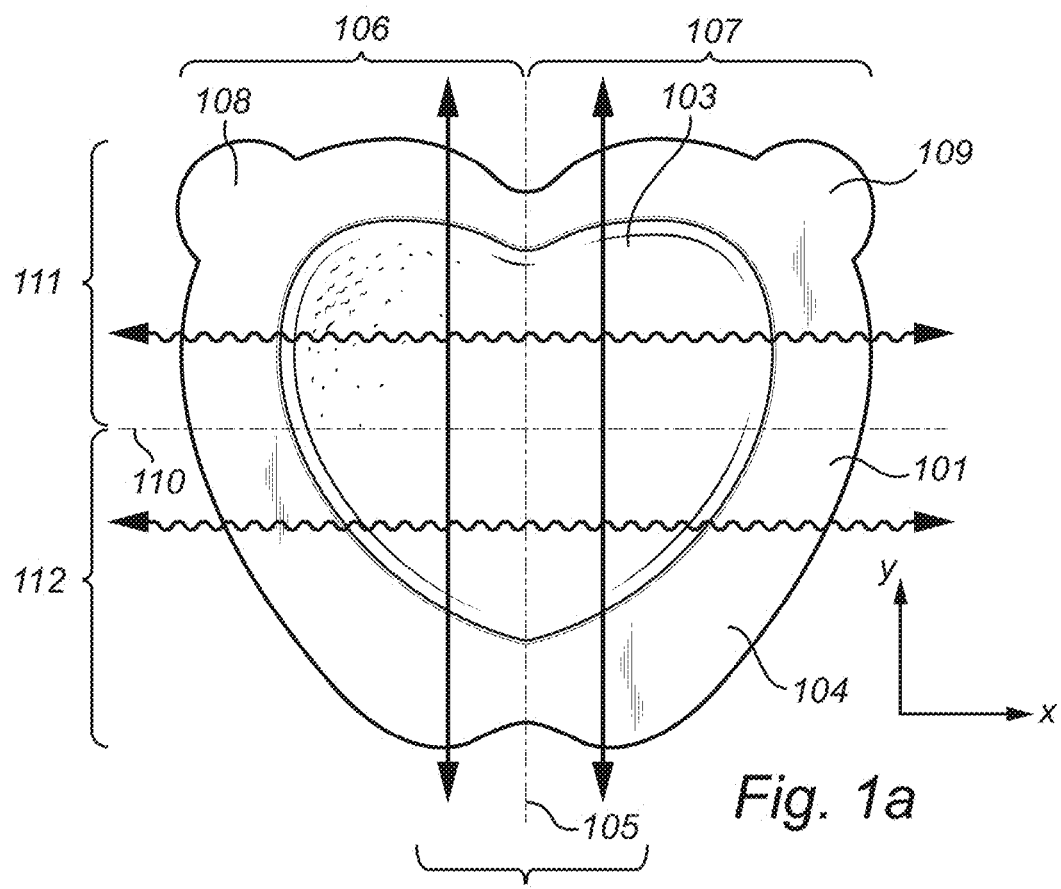
FIG. 1a illustrates a medical dressing according to the invention.

In the following, the embodiments of the invention will be described in further detail with reference to the illustrative figures attached hereto.

FIG. 1 illustrates a dressing for application to a contoured surface, such as the sacrum of a patient. The dressing has a central portion and a surrounding border portion and a lateral (x) and a longitudinal (y) extension and comprises a backing layer 101, an adhesive body contact layer 102 and a pad 103 arranged in the central portion between the backing layer 101 and the body contact layer 102. The backing layer 101 and the body contact layer 102 extend beyond the periphery of the pad 103 to define the border portion 104 along the contour of the pad 103. The pad 103 is symmetric about a longitudinal center line 105 and the dressing comprises a first lobed portion 106 on one side of the longitudinal center line 105 and a second lobed portion 107 on the other side of the longitudinal center line 105. The central portion has a tensile strength in the longitudinal (y) direction of at least 60 N, preferably at least 70 N at an elongation of 25%, as measured by the test method ASTM D 882-12, modified as described hereinafter.

As used herein, the term "body contact layer" means the layer that is in contact with the skin of a wearer. In the field of medical dressings, in particular, wound dressings, a film provided with an adhesive layer for adhering to the patient is often referred to as a wound contact layer. The present invention is primarily intended for pressure ulcer prevention, i.e. for use on a human body area which has no wound. Therefore, in this application the combined film and adhesive layer will be referred to as a body contact layer. However, it should be understood that although the primary use of the invention is pressure ulcer prevention, if nursing personnel decides to use it as a wound dressing, the body contact layer could be applied onto a wound.

As used herein, the term "lobed portion" means a curved or rounded portion of the dressing.

As used herein, the term "tensile strength at 25% elongation" refers to the tensile load when the dressing has been stretched 25% of its length. The tensile strength has been measured using the standard test method ASTM D 882-12, wherein the following specifications of the method were used: sample width: 50 mm, grip separation: 50 mm, speed: 100 mm/min and central portion of full product tested). The tensile strength is measured at an elongation of 25% since this elongation represents the stretch of the product in use; i.e. when exposed to friction and shear in bed-ridden conditions.

The present invention is based on the principle that in order to withstand the pressure and shear forces inflicted on a patient being bedridden during a period of time, the dressing should be stiff, i.e. have a high tensile strength in the direction by which the patient slides in bed. This way, skin cells and deeper tissue layer cells are protected from stretching, and thereby deforming. Sustained deformation of skin and tissue cells may affect the tissue in various ways; i.e. impaired cell metabolism resulting from vascular occlusion leading to ischemia, impaired membrane transport of the individual deformed cells, tears in-between cells, all of which may result in tissue and cell damage resulting in the formation of pressure ulcers.

It is important that the stiffness and the integrity of the dressing is maintained when the dressing becomes wet. Patients being bedridden are often warm and sweaty, and sometimes even incontinent. A dressing applied to the sacral region is therefore likely to become moist relatively quickly.

Therefore, in embodiments, the central portion of the dressing has a wet tensile strength in the longitudinal (y) direction of at least 50 N, for example at least 65 N, at an elongation of 25%, as measured by the test method ASTM D 882-12, modified as described hereinbelow.

As used herein, the term "wet tensile strength at 25% elongation" refers to the tensile load when the dressing has been stretched 25% of its length. The wet tensile strength has been measured according to the standard test method ASTM D 882-12, which has been modified as described hereinbefore, but adapted for measurements in wet conditions. In this test set-up, 3 ml of water was added as droplets over the surface of a central portion (area of 50×50 mm) of the dressing. The water was allowed to fully absorb into the products for at least 10 minutes.

Figure 2A:
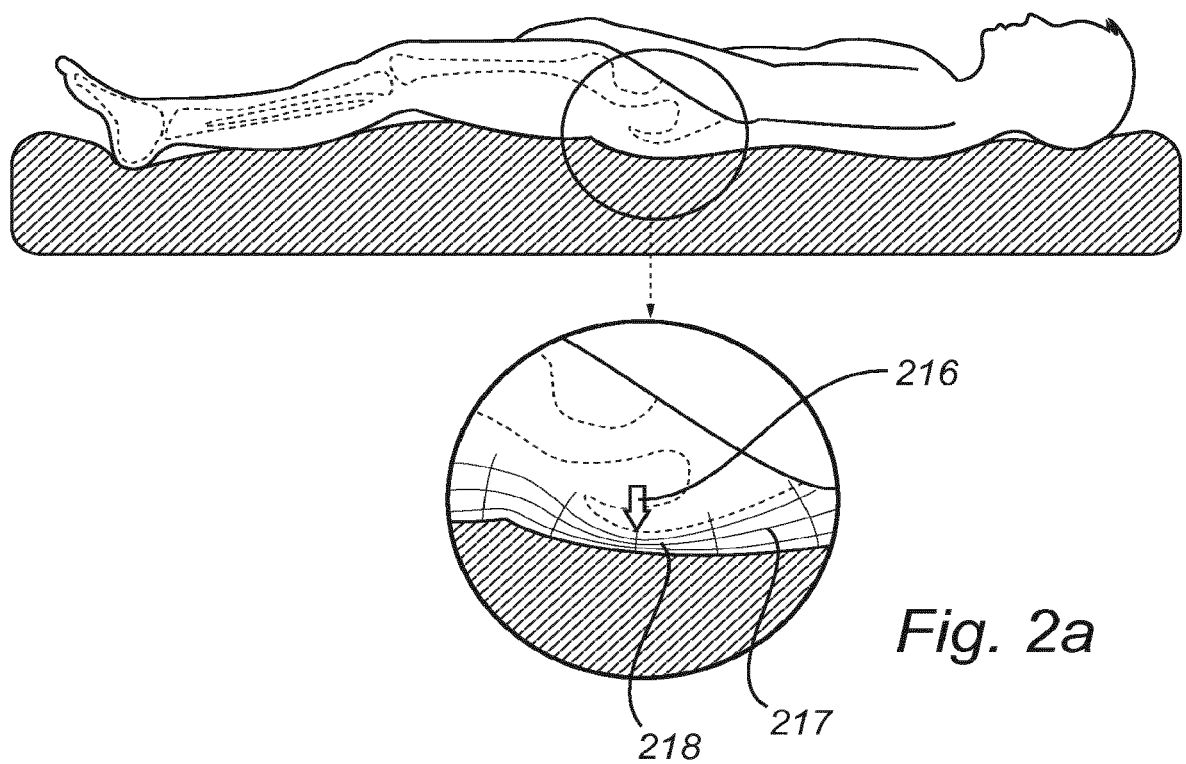
FIGS. 2a and 2b illustrate a bedridden patient exposed to pressure forces when no dressing is used (2a), and when a dressing of the invention has been applied to the sacrum region of the patient (2b).

The effects of the invention may be explained with reference to FIG. 2. FIG. 2a illustrates a patient lying down on a bed, and shows the pressure forces 216 exerted on the skin when no dressing is used. The soft tissue layers are represented by the lines 217. As can be seen, the individual tissue cells 218 in the area of the sacrum become compressed when exposed to sustained pressure. Individual soft tissue cells 218 may thus start to deform and deteriorate, which ultimately may lead to the formation of a pressure ulcer.

Figure 2B:
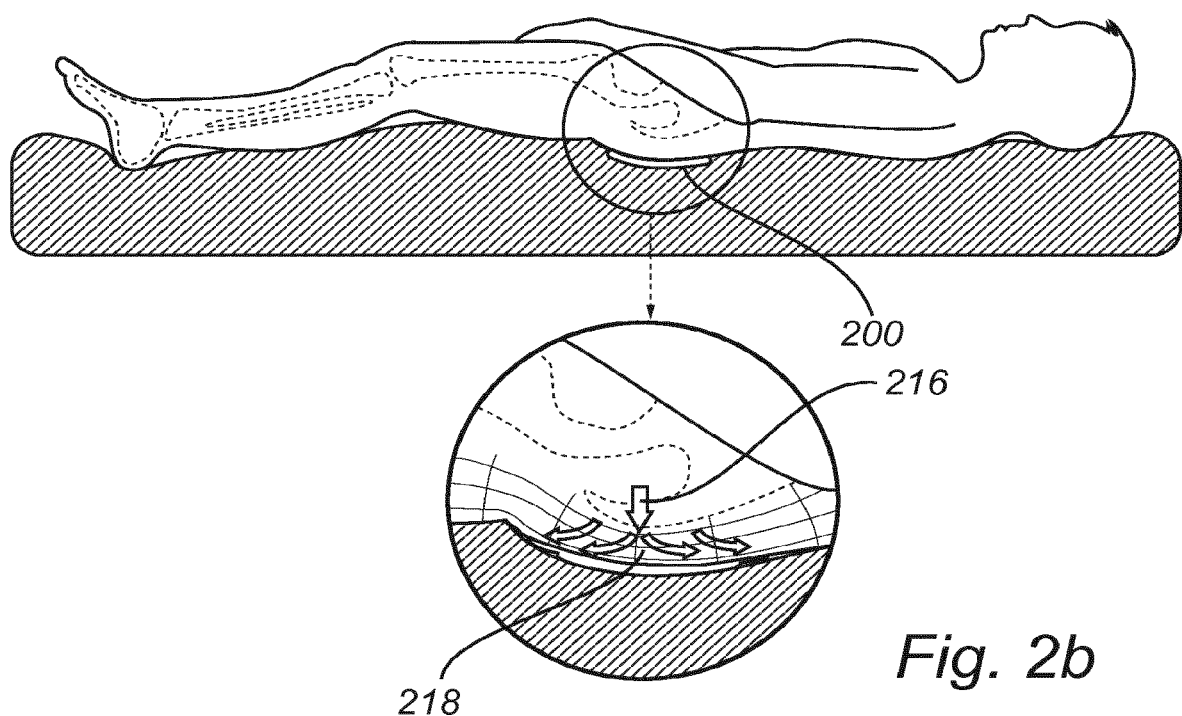

In FIG. 2b, a dressing 200 according to the invention has been applied to the sacrum region of the patient. When a dressing 200 is applied to the delicate skin of the sacrum region, the pressure forces 216 are absorbed by the dressing 200 and distributed symmetrically over a larger area. This leads to pressure re-distribution by reducing the magnitude of forces applied to the skin. The individual tissue cells 218 in the sacral region of the patient are therefore maintained relatively intact.

Figure 2C:
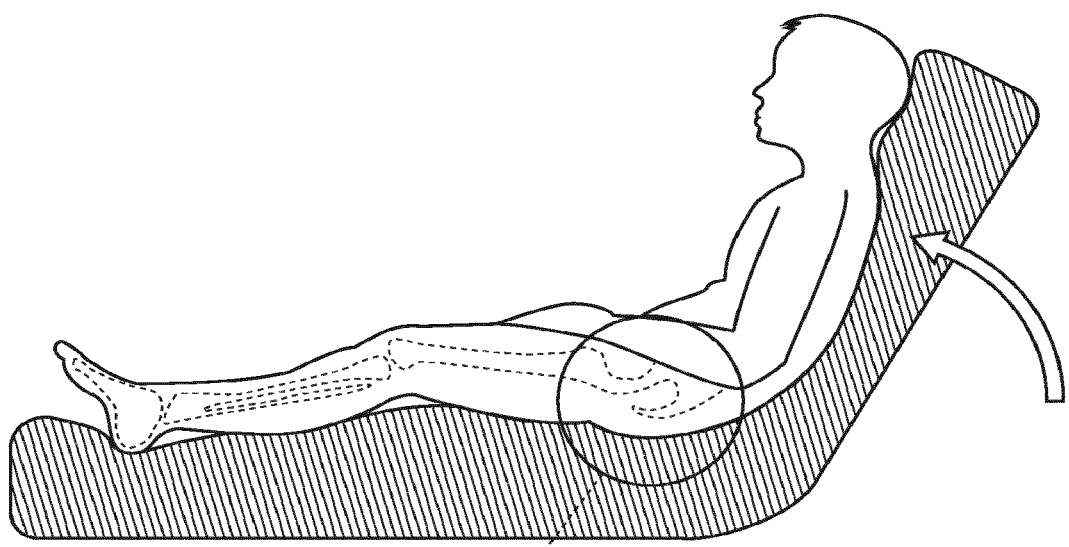
FIGS. 2c and 2d illustrates a bedridden patient exposed to pressure and shear forces when the head of the bed is tilted upwards when no dressing is used (2c), and when a dressing of the invention has been applied to the sacrum region of the patient (2d).

FIG. 2c illustrates the state where the head of an adjustable bed has been elevated and the patient has been placed in a more upright condition. The fragile skin and the underlying tissue of the bedridden patient is subject, not only to pressure and compression forces, but also to shear forces 219 resulting from friction as the patient slides in bed. The naked, moist skin rubs against the bed sheet and is subject to high shear forces 219. The individual tissue cells 218 are thus subject to both pressure and compression, while at the same time being stretched. This has a negative impact on the soft tissue, and the tissue cells 218 are more prone to deformation, which ultimately may lead to the formation of a pressure ulcer.

Figure 2D:
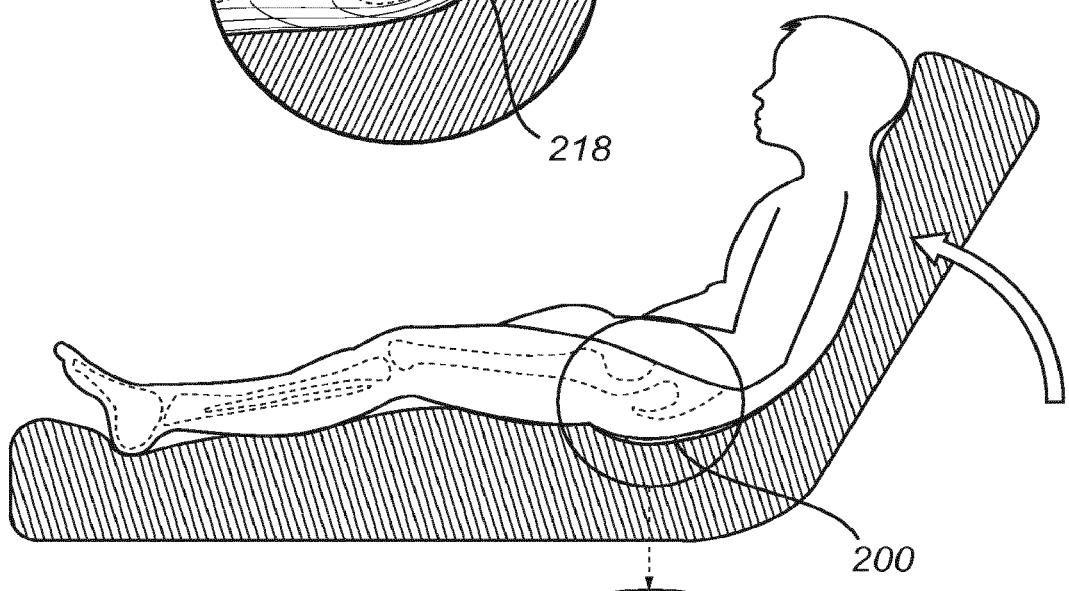

As illustrated in FIG. 2d, a dressing 200 of the invention is applied to the sacrum region of a wearer such that the stiff, longitudinal (y) direction corresponds to the direction of shear and stretch of tissue. In this case, the shear forces 219 are absorbed by the dressing since the dressing is stiff in the direction in which the patient slides in bed. Therefore, the stiff dressing "locks" the skin such that it does not stretch in the region where the dressing 200 is applied. The stretching of the skin may still occur at skin areas outside the dressing (which areas are less prone to deformation, and less at risk for pressure and shear). This way, pressure forces are separated from shear forces and the stress and stretch on skin cells and the underlying tissue cells 218 is minimized. In other words, the dressing 200 "translates" the shear forces and stretch of tissue to the skin outside the area of concern.

In embodiments, the tensile strength of the central portion of the dressing in is higher in the longitudinal (y) direction than the tensile strength in the lateral (x) direction. For example, the tensile strength in the longitudinal (y) direction may be at least 2.5 times higher, preferably at least 4 times higher than the tensile strength in the lateral (x) direction.

A dressing according to the invention may have anisotropic stretching properties, which means that the dressing has different stretching properties in the longitudinal (y) and the lateral (x) directions.

The term "stretch", as used herein, refers to the lengthening of a dressing or a material in a particular direction by applying a tensile force on the material in that direction. As the term is used herein, once the tensile force on the dressing or the material is removed, the material will return to its original dimension with no substantial change in the dimension of the material in the direction that the material was stretched.

The dressing is advantageously more stretchable in the lateral (x) direction. A bedridden patient at risk of developing pressure ulcers must be turned and repositioned at regular intervals. It is therefore important that the dressing conforms to this lateral movement and stays on the skin. If the dressing is too stiff in this direction, the dressing may fall off easier.

The differences in stretchability of the dressing are illustrated by the arrows in FIG. 1a.

In embodiments, the adhesive body contact layer 102 of the dressing covers at least 60% of the surface of the pad 103. Suitably, the adhesive body contact layer 102 covers at least 75% of the surface of the pad 103.

It is beneficial to have an even distribution of adhesive over the surface of the pad 103 in order to keep the dressing in place during use. Also, a greater coverage of adhesive on the surface of the pad aids in preventing undesirable friction forces which could form between the skin and the dressing as a patient slides in bed. The adhesive body contact layer 102 has a body facing surface; i.e. a surface oriented towards the skin of the wearer, and a non-body facing surface, i.e. a surface oriented opposite to the adhesive surface when fitted to a wearer. The adhesive body contact layer 102 may comprise a film covered by an adhesive layer (not shown). The adhesive used should be skin-friendly and permit the removal of the dressing without causing damage to the skin. It should also have a strong adhesive effect to enable a prolonged time of use. Examples of suitable adhesive coating materials include, but are not limited to, silicone gels, hot melt adhesives, acrylate adhesives, polyurethane gels, and hydrocolloid adhesives. In some embodiments, the adhesive is comprised of a material that is non-irritating to the skin, e.g. a silicone gel. Examples of suitable silicone gels include the two component RTV systems, such as Q72218 (Dow Corning), and SilGel 612 (Wacker Chemie AG) mentioned herein, as well as NuSil silicone elastomers. In embodiments of the invention the adhesive may comprise a soft silicone gel having a softness (penetration) of from 8 to 22 mm, e.g. from 12 to 17 mm, as measured by a method based on ASTM D 937 and DIN 51580, the method being described in European Patent Application No 14194054.4. The thickness of the adhesive layer is preferably at least 20 µm. The film onto which the adhesive layer is applied may be comprised of a thin plastic film, or a laminate comprising a thin plastic film. Suitable materials for the film include, but are not limited to breathable polyolefin based films (such as polyethylene), polyamide, polyester polyurethane, and silicone. A suitable material for use as the film is a thin polyurethane film. For example, the film of the body contact layer 102 may be a polyurethane film having a thickness from 15 and 100 µm, e.g. from 40 to 80 µm, preferably from 45 to 60 µm.

The adhesive body contact layer 102 may be perforated with perforations 116. The perforations 116 typically extend through the body contact layer. The perforations 116 allow for a quick absorption into the pad 102 without compromising the tight fit to the skin provided by the adhesive layer, arranged to be in contact with the skin. The perforations 116 may have different shapes and densities along varying regions of the body contact layer 102, and may be arranged in a regular or irregular pattern.

The border portion may have a tensile strength of between 3.5 and 10 N, preferably between 4 and 6 N at an elongation of 25%, as measured by the standard test method ASTM D 882-12.

These characteristics are important for inspection of the skin. A caregiver must regularly inspect the skin to study any differences in skin appearance, which may indicate that a pressure ulcer is about to develop. In order to improve the handling; i.e. the application and re-application of the dressing onto the skin, it is important that the border portion 104 has sufficient rigidity such that it does not curl or fold against itself during inspection. At the same time, it must not be too rigid as it should be able follow and conform to contoured surfaces of the skin, e.g. the sacrum.

The border portion 104 of the dressing is formed from the backing layer 101 and the body contact layer 102. The body contact layer 102 is typically co-extensive with the backing layer 101, and has the same outer dimensions. Hence, both the backing layer 101 and the body contact layer 102 define the border portion 104 along the contour of the pad 103. Typically, the border portion forms a closed path around the contour of the pad. The backing layer 101 and the body contact layer 102 are bonded to each other in those areas of both layers that extend beyond the periphery of the pad 103. In order to achieve sufficient adhesion properties, the border portion 104 has a width of 5 to 50 mm and extends along the contour of the pad 103. A smaller sized dressing may have a smaller border portion than a larger sized dressing. Preferably the border portion 104 has a width of 10 to 25 mm and extends along the contour of the pad 103. This allows for easy handling and application of the product while still maintaining sufficient adhesion upon application.

The backing layer 101 of the dressing is preferably made of a material that can reduce friction when a patient slides in bed. Reducing friction is an important aspect, since friction is the source of shear, and reducing shear is important in preventing the onset of pressure ulcers. The backing layer acts as a "sliding layer" and prevents the translation of friction into shear forces.

The backing layer preferably has a friction coefficient of less than 1.5 as measured by the standard test method ASTM D 1894-14 (measured against cotton).

More suitably, the backing layer has a friction coefficient between 0.4 and 1, as measured by ASTM D 1894-14.

It is desirable to have a low friction coefficient in order to reduce the friction between the dressing and the bed sheet. Such friction may give rise to harmful shear forces on the skin. The backing layer 101 may instead acts as a "sliding layer" such that the friction is reduced between the skin and the bed.

The backing layer 101 should also be breathable such that moisture and heat can evaporate from the dressing. The backing layer 101 may be a thin film, sheet or membrane that is vapour permeable and waterproof. Examples of suitable materials for the backing layer 101 include, but are not limited to polyurethane, polyethylene or polyamide films, silicone films, polyester based nonwoven materials, and laminates of polyester-based nonwoven materials and polyurethane films. A suitable material for use as a backing layer is polyurethane. For example, the backing layer 101 may be a polyurethane film having a thickness of from 5 to 40 µm, e.g. from 15 to 25 µm.

The backing layer 101 may be bonded to the pad 103, for example, via an adhesive such as a pressure sensitive adhesive (e.g. an acrylic adhesive). The backing layer 101 is bonded to the body contact layer 102 in those parts of the backing layer 101 that extend beyond the wound pad 103. The adhesive may be a thin acrylic adhesive.

In exemplary embodiments, the pad 103 comprises a material that yields a pressure-relieving effect. Suitably, the pad 103 is an absorbent pad. In embodiments, the pad is a multilayered pad. For example, the pad may comprise two or more layers having different properties.

Suitably, the pad 103 comprises a first layer and a second layer; the first layer being arranged between the backing layer and the second layer of the pad, wherein the first layer has a higher affinity for liquid than the second layer. This construction is believed to be beneficial when it comes to microclimate. Factors such as stress, fever, poor nutrition and circulatory status and various treatments may trigger a stress reaction, and cause excess sweating. Heat and excess moisture may accelerate cell metabolism of the cells and if already exposed to deformations through pressure and shear this is likely to result in accelerated cell death. Since the first layer has a higher affinity for moisture than the second layer, moisture will move to the first layer, and thereafter evaporate from the backing layer 101. This way, there will not be an accumulation of body liquids close to the skin, but the second layer may be kept relatively dry.

The second layer may act as a liquid acquisition layer and/or liquid distribution layer, and may be made of foams and/or cellulose based materials. For example, a polyurethane foam may be used. In some embodiments, the second layer acts as a wicking or spreading layer and may comprise a nonwoven material, e.g. viscose, polyester or blends thereof.

The first layer may comprise a superabsorbent material, e.g. superabsorbent polymers (SAP) or superabsorbent fibers (SAF). Alternatively, the first layer comprises an absorbent foam material.

Figure 1B:
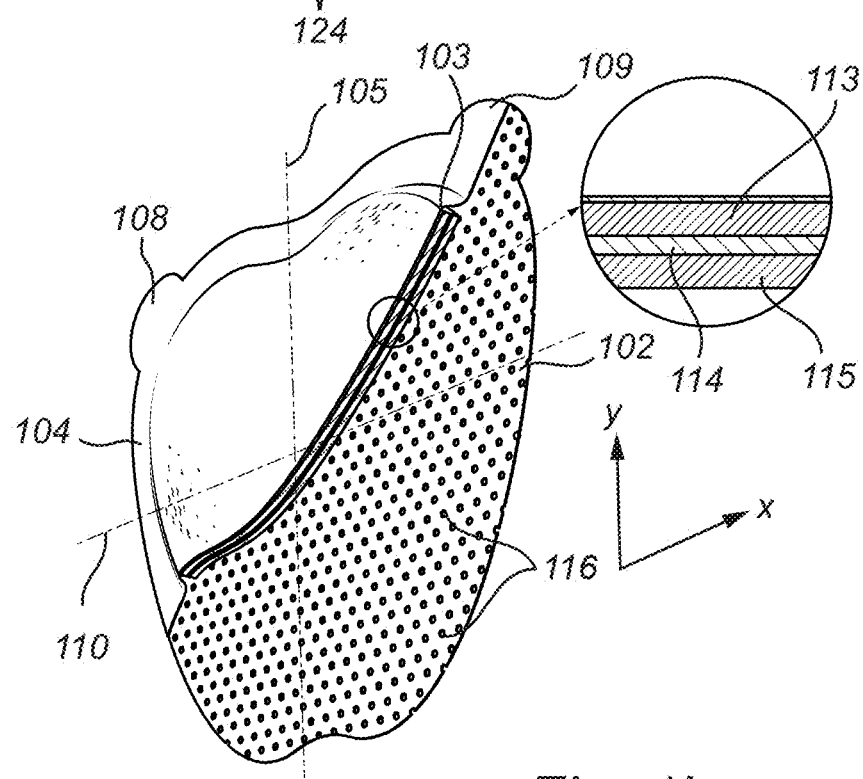

As illustrated in the zoomed part of the pad in FIG. 1b, the pad 103 may comprise three layers; i.e. a first layer 113, a second layer 114 and a third layer 115. In this case, the second layer 114 is arranged between said first 115 and third 113 layers. The first layer 113 may serve as a liquid absorption layer, the second layer 114 may serve as a liquid distribution or wicking layer and the third layer 115 may serve as a liquid acquisition layer. The layers may be at least partially laminated together, but suitably allows some movement within the layer structure, when rubbed.

The material of the dressing, and the individual layers (if present) may be selected or modified to contribute to the stiffness of the dressing in the longitudinal (y) direction. There are various ways by which this can be achieved. For example, the dressing may comprise a fibrous web containing a substantially homogenous arrangement of fibers generally aligned along the longitudinal (y) direction of the dressing.

The desirable strength properties may also be achieved by embedding woven threads in one layer of the dressing. This way, a reinforced textile matrix may be obtained. The threads will act as reinforcement in the direction which they are placed, adding to the tensile strength of the material.

Furthermore, a relatively stretchable material such as for example a foam may be made stiffer in the longitudinal (y) direction through the incorporation of stiff threads or fibers. Alternatively, strips of hotmelt glue may be applied on top of the elastic material such that the material becomes stiffer in one (i.e. the longitudinal) direction.

It is of course equally conceivable to modify a material that is stiff in all directions such that it becomes more stretchable in the lateral (x) direction, but still maintains its stiffness in the longitudinal (y) direction. This may be achieved by e.g. directional cutting; i.e. cutting the fibers in the longitudinal direction such that only the fibers aligned in the lateral (x) direction will be cut.

In at least some exemplary embodiments, the border portion 104 is substantially heart shaped such that the first and second lobed portions 106 and 107 form part of the lobed upper sides of a heart shape.

Suitably, the first and second lobed portions are separated by a forked portion 124 which replaces the pointed lower part of a heart shape.

The shape of the medical dressing is adapted to fit to the sacral region of a human body. The forked portion allows for an improved stay on ability in the gluteal cleft region. It is important that the dressing remains adhered in this region since otherwise body fluids (for example as a result of incontinence) may enter into the dressing and impair the adhesion to the skin.

Figure 3:
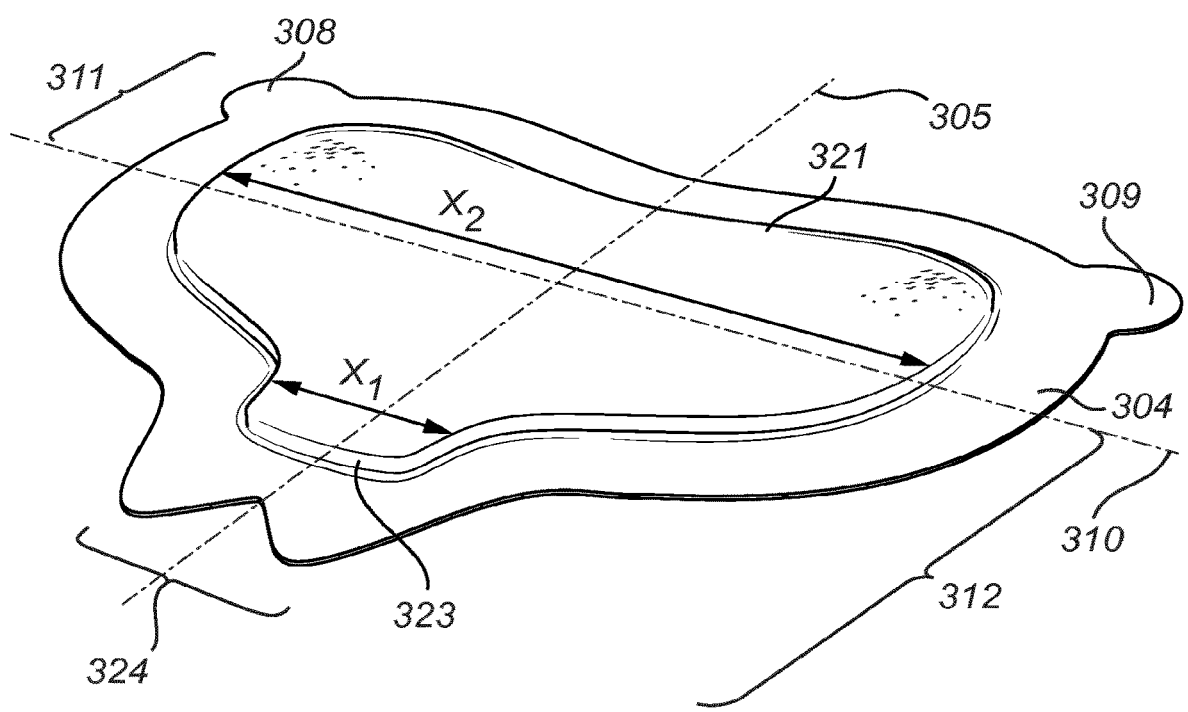
FIG. 3 illustrates a medical dressing according to at least one exemplary embodiment of the invention.

An exemplary embodiment of the dressing of the invention is illustrated in FIG. 3, in which the pad is divided by a lateral center line 310 into an upper pad region having an upper lateral edge 321 and a lower pad region having a lower lateral edge 323. The width, x1, of the lower lateral edge 323 is between 10 and 40% of the maximum width, x2, of the pad in the lateral (x) direction.

The maximum width, x2, of the pad dressing is typically in the range of from 12 to 30 cm, e.g. from 15-20 cm. The width, x1, of the lower lateral edge may be in the range of from 1 to 7 cm, e.g. from 2 to 4 cm, depending on the size of the dressing.

The pad has a more narrow width in the lower region of the dressing in order to conform with the gluteal cleft and to provide for protection in this region. The shape of the pad is designed to cover the coccyx of a human body.

As illustrated in FIG. 3, the forked portion 324 comprises a protrusion on either side of an interstice located coaxially with the longitudinal center line.

In embodiments of the invention, the dressing may comprise a gripping tab 308, which tab is coplanar with and projects outwardly from the border portion 304 of one of the lobed portions. In this connection it should be understood that inwardly means a direction towards the inner perimeter of the border area, i.e. a direction towards the pad, while outwardly is an opposite direction.

The gripping tab 308 guides the caregiver to lift the dressing, inspect the skin underneath the dressing, and to thereafter re-apply the dressing onto the skin (in case the skin looks good).

As illustrated in FIGS. 1 (where a first gripping tab is denoted 108 and a second gripping tab is denoted 109) and 3, the gripping tab 308 is typically made in one piece with, and projecting outwardly from the border 304. The gripping tab 308 may be made of the same materials as the border portion 304, e.g. it may be made from the backing layer and the body contact layer. Hence, the border portion 304 may extend uninterrupted from the border to the gripping tab 308. This may be beneficial from a manufacturing perspective. However, in at least some exemplary embodiments the gripping tab may be made from a different (or same) material and attached to the border portion 304. Alternatively, the gripping tab 308 may be reinforced by an additional material layer, e.g. a nonwoven or a film to make the tab stiffer and easier to grasp. In embodiments, the entire border portion 304, or at least parts thereof may be reinforced by applying an additional material portion at the border portions.

The gripping tab 308 may be covered by the adhesive body contact layer for adhering the tab to skin surrounding the area of prevention. This may be advantageous to avoid accidental removal forces being applied to the gripping tab/tabs, bearing in mind that a gripping tab is more likely to rise relative to the rest of the product if it is not adhered to the skin. If the gripping tab 308 is formed in one piece with the border portion, it may also be advantageous from a manufacturing point of view to share the adhesive layer of a body contact layer of the border portion. It is also conceivable to have no adhesive layer underneath the gripping tab 308 of the dressing.

The gripping tab may be of a variety of shapes, including square, rectangular, triangular, or rounded. The size and the dimensions of the gripping tab may also be adjusted. The gripping tab should be sized to be easy to grip with a thumb and another finger. In the case of a rounded or semicircular gripping tab, the radius may be in the range of 5 mm to 20 mm, e.g. 8 mm to 15 mm. According to at least one exemplary embodiment the surface area of the or each gripping tab is between 40 and 600 mm$^2$, suitably between 100 and 350 mm$^2$. The size of the tab is of course dependent on the size of the dressing. The tab should be of a size that guides the user to see it, and to grasp it properly for inspection Since the inspection of the skin typically takes place where the patient is lying on the side in the bed, it is beneficial to have at least two gripping tabs such that the caregiver can lift the dressing from either side of the back or the dressing.

In embodiments, the gripping tab is a first gripping tab 308, and the dressing further comprises a second gripping tab 309 that is coplanar with and projects outwardly from the second lobed portion.

The dressing may be divided by a lateral center line 310 (same lateral center line that separates the upper and lower regions of the pad) into an upper region and a lower region, the gripping tab(s) 308 and 309 being arranged in the upper region of the dressing. (In FIG. 1, the upper and lower regions of the dressing are denoted 111, and 112, respectively).

The lower region of the dressing should preferably stay adhered to the skin during inspection of the skin. Otherwise, wrinkles at the border portion of the gluteal cleft region may occur.

Suitably, the distance between the outer perimeters of the first and second gripping tabs 308, 309, respectively, is larger than the largest extension of the remaining part of the dressing in the (x) lateral direction.

This arrangement allows for the forces applied to the border portion when the dressing is opened up and pulled downwards to be distributed evenly over the border. This way, the border portion 304 can be held stably during inspection, and is prevented from collapsing or folding against itself.

Figure 4A:
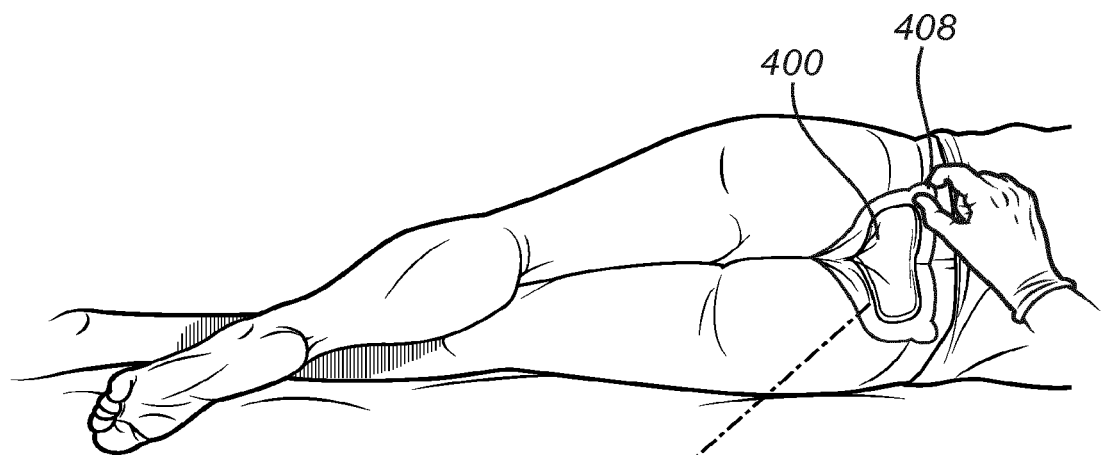
FIG. 4a shows a medical dressing according to at least one exemplary embodiment of the invention, the dressing having been applied to the sacrum region of a human body.
Figure 4B:
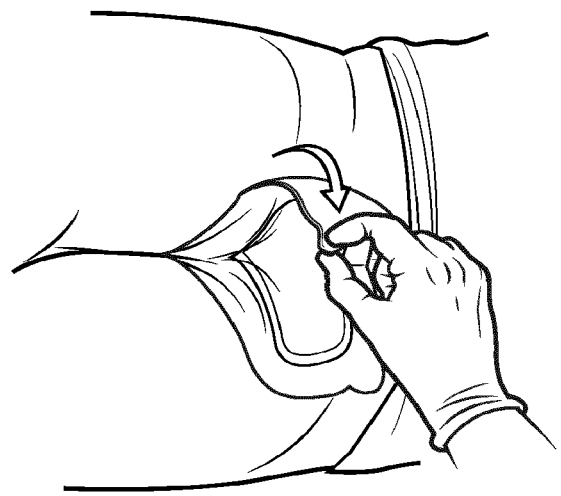
FIG. 4b is a detailed view of the dressing in FIG. 4a, illustrating inspection of the skin of the wearer.

FIG. 4 illustrates a patient lying on the side, which is often the case for patients at risk of developing pressure ulcers. The tab 408 guides the caregiver to the correct spot on the dressing. The caregiver may then use his hand to lift the tab 408 and partially remove the dressing 400 from the skin and inspect the skin underneath (FIG. 4b). Once the skin has been checked, the dressing may be re-applied to the skin or taken off if needed.

In embodiments, the backing layer comprises a functional enhancement print, wherein the functional enhancement print is asymmetric in the lateral (x) and longitudinal (y) directions in a non-stretched state.

The functional enhancement print visually communicates to the user, the differences in functionality of the dressing; i.e. indicates the difference in stretching properties in the lateral, and longitudinal direction, respectively. It also aids in guiding the user to select a particular dressing for prevention purposes, and to distinguish it from dressings more suitable for wound treatment purposes.

As illustrated in FIG. 5, the functional enhancement print may be a continuous print selected from a lattice of ellipses, rectangles and lines intersecting as crosses.

In another aspect, the invention relates to a dressing as described hereinbefore for use in the prevention of pressure ulcers.

However, although the primary use of the invention is for prevention, such a dressing may also be used in the treatment of pressure ulcers or wounds. In yet another aspect, the invention relates to a kit that comprises a dressing as described hereinbefore and at least one dressing suitable for application onto the heel.

For a person being bedridden for a long time, the vital parts to protect are the sacrum and the heels. For example, the kit may comprise a dressing according to the present invention and two dressings for application to the heel. It is also conceivable to include additional products in such a kit, for example creams, cleansing solutions etc. A kit according to the invention may also include a turning and positioning mattress which may be used when patients are unable to be repositioned or are likely to undergo lengthy surgical procedures. Additional dressings may also be comprised in such a kit, e.g. dressings suitable for use on the knees, hips, chest etc.

The dressing 100 may also comprise a release liner (not shown) releasably attached to the body contact layer 102. As used herein, the term "releasably attached" means that the release layer may be peeled away from the rest of the dressing by hand. The removable portions of the release liner are releasably connected to each other meaning that they are connected such that the portions remain connected absent a separation force applied to one or all of the portions, and where the portions are capable of being separated upon the application of a separation force. The release liner acts as a barrier that can protect the sterility of dressing including all of its layers before the dressing is used. The release liner may comprise three separate, releasably connected removable portions.

The release liner may be made of any of a variety of suitable materials known in the art, e.g. polyethylene, polyester, polypropylene and silicone coated paper. For example, the release liner may be a polyethylene film having a thickness in the range of from 30 to 300 µm, e.g. from 50 to 150 µm.

The dressing of the invention is not restricted for mere purpose of preventing pressure ulcers, but may also be used in the treatment regimen of such ulcers or sores.

Tensile Strength Measurements

The tensile strength was compared between two dressings according to the present invention, references A and B, and two dressings according to prior art. Reference C was Allevyn® Life Sacrum and Reference D was Aquacel foam Sacrum, two products which are commercialized by Smith&Nephew, and Convatec, respectively, and which are dressings that are to be applied to the sacrum region. The reference dressings A and B were similar in construction; i.e. they both comprised: a wound contact layer (polyurethane film coated with a silicone adhesive), a backing layer (polyurethane film), and a pad comprising three different layers laminated together (a polyurethane foam layer, a nonwoven liquid distribution layer and an absorbent layer comprising superabsorbent fibres). The reference dressings differed in the composition of the liquid distribution layer. The liquid distribution layer of reference A was a 40 gsm spunlace nonwoven comprising viscose and polyethylene (70:30). The nonwoven of dressing A had a tensile force at break of 60 N and an elongation at break of 20% in the longitudinal (y) direction, and a tensile force at break of 17 N, and an elongation at break of 120% in the lateral (x) direction. The liquid distribution layer of reference dressing B was a 70 gsm spunlace nonwoven comprising viscose and polyethylene (70:30). The nonwoven of dressing B had a tensile force at break of 110 N and an elongation at break of 40% in the longitudinal (y) direction, and a tensile force at break of 85 N and an elongation at break of 60% in the lateral (x) direction. The dry tensile strength of the dressings A-D was measured in accordance with the standard test method ASTM D 882-12, modified as follows. Strips of the central portions of the products were cut out (width: 50 mm) and used for testings. The grip separation used in the method was 50 mm, and the speed was 100 mm/min. The tensile load was measured at different elongations and three specimens were used for measurements in the lateral (x), and longitudinal (y) directions, respectively.

The wet tensile strength was measured according to the same standard test method ASTM D 882-12, but was slightly modified for measurements in wet conditions. In this test set-up, 3 ml of water was added as droplets over an area of the central portion of the dressing (50×50 mm). The water was allowed to fully absorb into the products for at least 10 minutes.

Table 1 illustrates the tensile strength in dry and wet conditions for both the lateral (x) and longitudinal (y) directions, at an elongation of 25%. This elongation is relevant for measurements as it represents the stretch of the product in use; i.e. when exposed to friction and shear in bed-ridden conditions.

TABLE 1

| Reference | Tensile strength (N) - longitudinal (y) direction | | Tensile strength (N) - lateral (x) direction | |
|---|---|---|---|---|
| | Dry | Wet | Dry | Wet |
| A | 92.5 | 72 | 13.7 | 11.3 |
| B | 110 | 84 | 21 | 15 |
| C | 36.3 | 36.7 | 61.3 | 38.2 |
| D | 22.9 | 9.2 | 46.4 | 9.9 |

As can be seen in table 1, reference samples A and B have a high tensile strength in the longitudinal (y) direction, and the tensile strength remains high even when the product has become wet. The liquid distribution layer acts as a "reinforcement layer" and serves to maintain the structural integrity and stiffness of the dressing, even when it becomes wet. This characteristic of the dressing contributes to "locking" of the skin cells and protecting the skin from deformation and shear forces.

Reference samples C and D on the other hand, are stretchable in the longitudinal (y) direction, and cannot support or prohibit the stretching of the skin to a sufficient degree. Furthermore, these dressings are stiffer in the lateral (x) direction of the dressings, which is believed to be a disadvantage for the purposes of stay-on ability to the back of a patient when the patient is repositioned in bed.

FIG. 6 illustrates the tensile curves for the dressings A, B, C, and D and the force required to stretch the dressings to different degrees. FIG. 6a represents the tensile curves for the longitudinal (y) direction in dry condition, whereas FIG. 6b shows the tensile curves in wet condition (longitudinal direction). FIG. 6c illustrates the tensile curves for the lateral (x) direction in dry condition, and FIG. 6d shows the tensile curves for wet conditions (lateral direction).

Figure 6A:
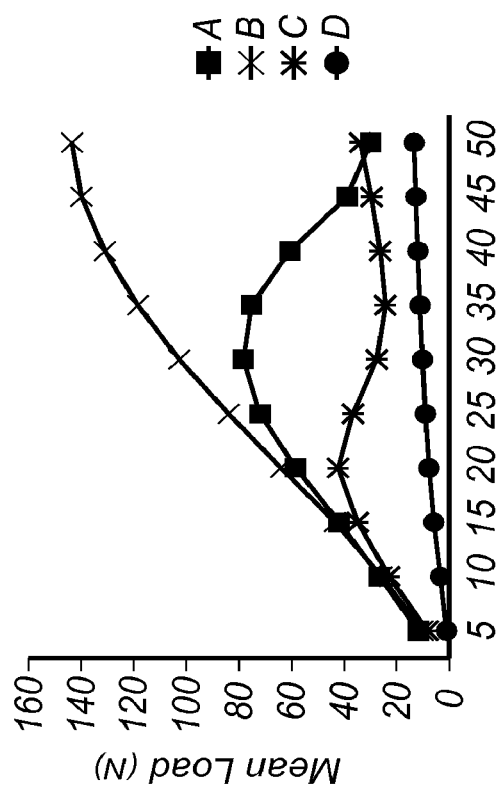
FIGS. 6a-b illustrate the tensile curves of two dressings according to the present invention compared to prior art dressings measured in the longitudinal (y) direction in dry (6a) and wet (6b) conditions.
Figure 6B:
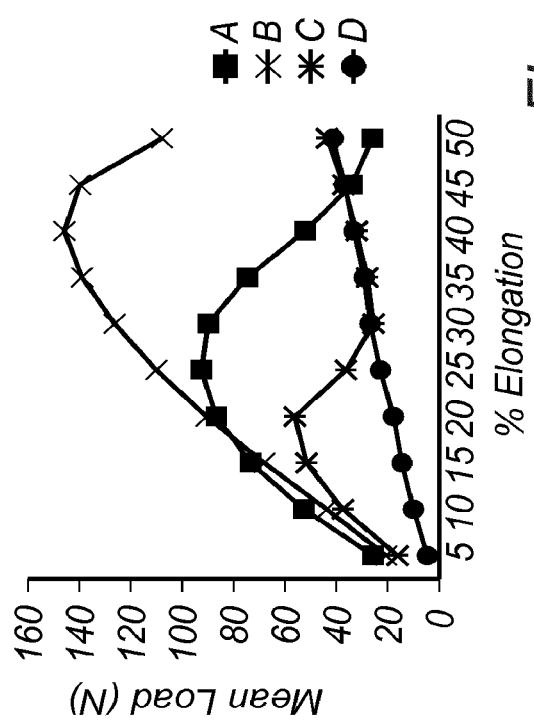

As can be seen in FIGS. 6a and 6b, dressing C deteriorates fast, and has lost all of its integrity at 20% elongation. This allows the tissue to stretch in the longitudinal direction, which is unfavourable for the purposes of pressure ulcer prevention. Dressing D does not withstand much load, and is very stretchable.

Dressings A and B withstand high forces at 20-25% elongation, and the stiffness is maintained in wet conditions.

Figure 6C:
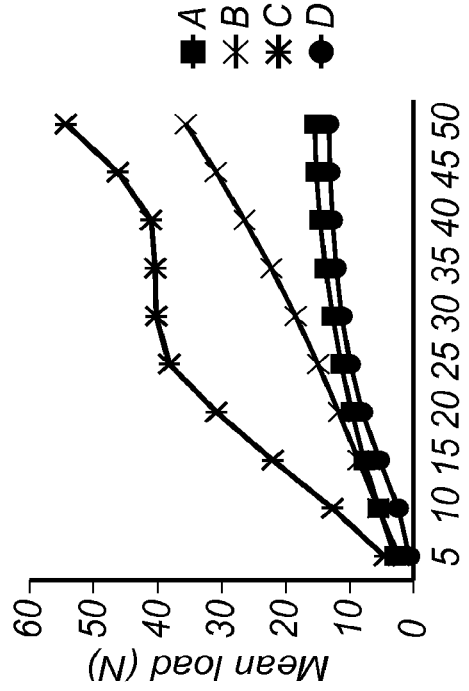
FIGS. 6c-d illustrate the tensile curves of two dressings according to the present invention compared to prior art dressings measured in the lateral (x) direction in dry (6c) and wet (6d) conditions.
Figure 6D:
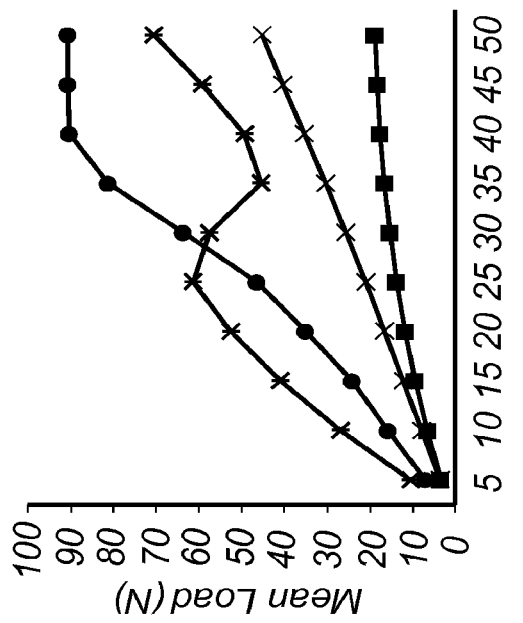

As can be seen in FIGS. 6c and d, the dressings of the invention are stretchable in the lateral (x) direction, and this is advantageous for stay-on purposes and ability to conform to the contoured skin when for instance the patient is repositioned in bed.

Finite Element (FE) Modelling

The mechanisms leading to pressure injuries are not fully understood. Pressure maps can give information on pressure present at the skin surface but does not inform on the behaviour inside the soft tissues, at the origin of damage. Therefore, the Finite Element (FE) method offers a great alternative to study the biomechanisms of action of pressure ulcers.

The FE method is a numerical and computational technique used to solve multiphysic problems by solving partial differential equations upon different types of discretizations. The FE method subdivides a large problem or large 3D model into smaller parts called finite elements. The analyses are performed within each elements and the assembly gives a solution to the entire problem.

The workflow for a FE analysis can be explained as follows: creation of a 3D model constituted of finite elements, definition of the material properties of the model, definition of the boundary conditions and loadings to apply to the model according to the problem, computational solving of the problem, and analysis of the results through visualization and calculations.

Finite Element (FE) Settings and Effect of Inventive Dressing

In order to understand the effect of the stiffness in the longitudinal (y) direction of the dressing, finite Element (FE) models of a pelvis and of a dressing according to the invention were created and analyses were performed to study the effect of pressure and stresses on the skin and in deep tissue layers. The volunteer was a non-smoker healthy adult male of 31 years at the time of the study (year birth 1984, length: 183 cm, weight: 77 kg).

The dressing according to the invention was created from technical CAD drawings and was designed to match the stiffness in the longitudinal (y) direction as defined in claim 1. A comparative dressing having a low tensile strength in the longitudinal (y) direction was also designed (representing 5% of the tensile strength of the invention). The FE model of the dressings contained 20 000 tetra elements.

The FE model of the pelvis was segmented from MRI scans of the pelvis in order to insure the best anatomical accuracy. Bones and soft tissues were represented in the model. The FE model prepared in ANSA 16.0.1 (BETA GAE) contained about two millions tetra elements. The soft tissues were represented as non-linear materials, the bones as rigid body. The deformation of the soft tissue caused by compression from the body weight has been used to validate the FE model and its material properties with the solver ABAQUS 14.0 (DASSAULT SYSTEM). The validation was carried out by comparing the thickness of the soft tissues before and after compression between the model and the MRI data.

The deformation of the soft tissue was performed by simulating a clinical setting where a patient is lying on a mattress. A soft mattress (30 kPa) is added under the pelvis and the equivalent of the body weight is applied to induce contact and compression of the pelvis on the mattress. Three different models were used to study the effect of tissue compression of the pelvis:

(I): Model of the pelvis without any dressing
(II): Model of the pelvis with a dressing according to the invention
(III): Model of the pelvis with a dressing having a low tensile strength in the longitudinal (y) direction.

Figure 7A:
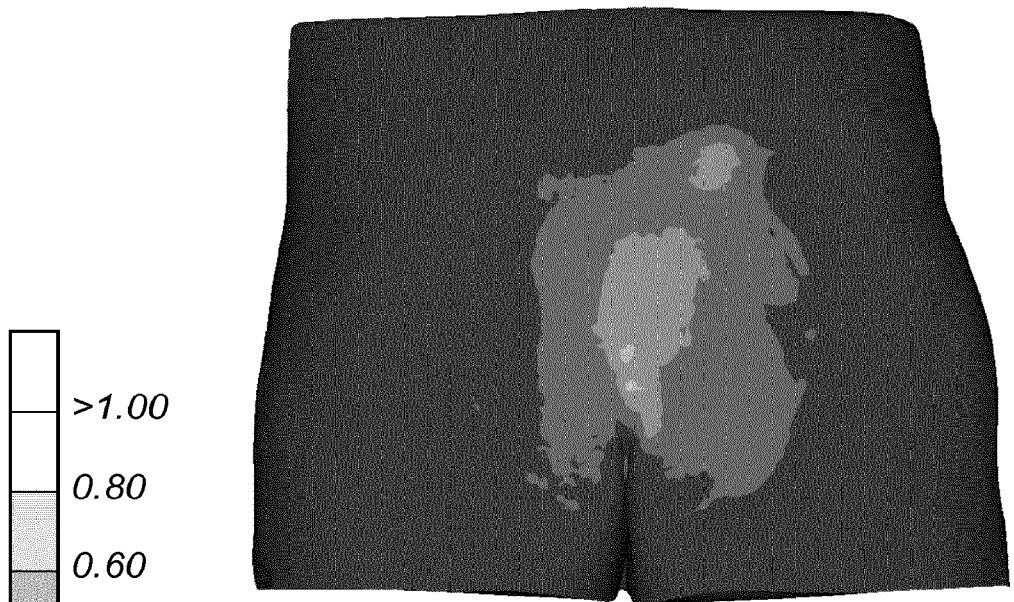
FIG. 7 illustrates images obtained from FE modelling of the sacrum region after exposure to pressure and compression when no dressing is used (FIGS. 7a and 7b) and when a dressing according to the invention has been applied (FIGS. 7c and 7d).
Figure 7B:
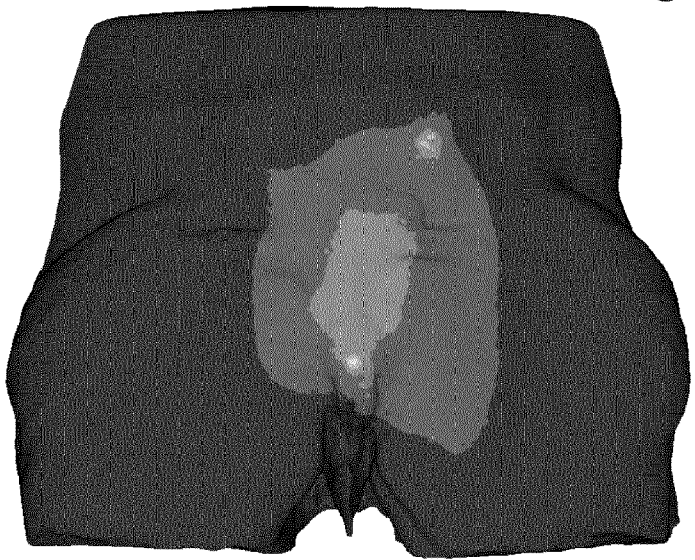
Figure 7C:
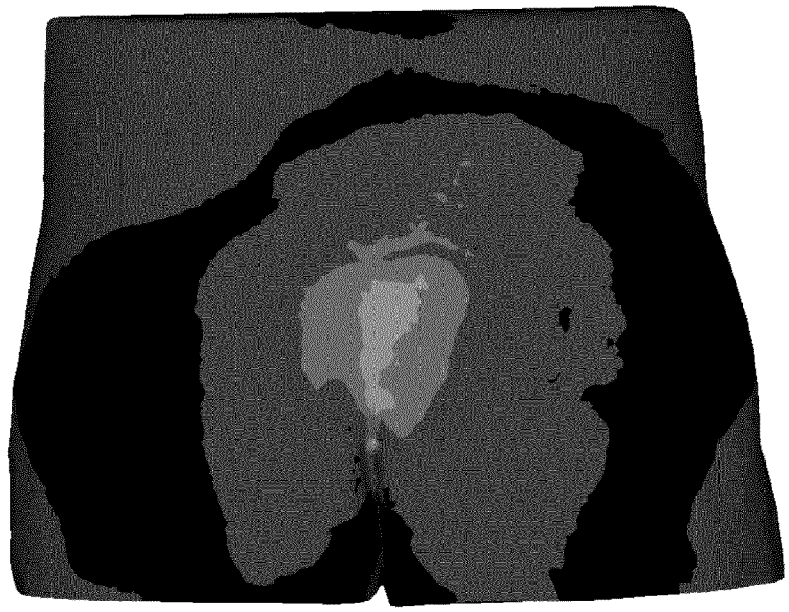
Figure 7D:
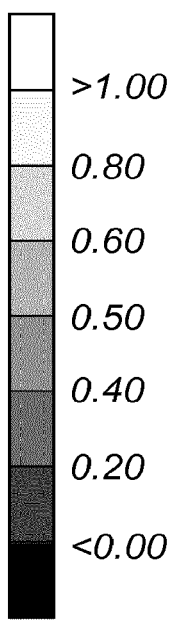
Figure 7D:

In order to facilitate the comparisons, the values were normalized with the higher pressure range values found for model I. FIG. 7 illustrates the effect on the soft tissue of the sacrum region when exposed to pressure and compression. FIG. 7a shows the effect of model I at the skin, and FIG. 7b illustrates the same model's effect at the muscle (no dressing used). FIGS. 7c and 7d show the effect of a dressing according to the invention at the skin, and at the muscle, respectively. The white spots in FIGS. 7a and 7b show the areas with highest pressure. The maximum pressure in model I is higher than the maximum pressure in model II, indicating that the dressing according to the invention may decrease the stresses in soft tissue.

Moreover, the area at the skin and at the muscle with pressure higher than 0.6 is smaller when a dressing according to the invention is used (model II) indicating that it has the positive effect of decreasing the area exposed to high pressure, both at the skin and in deeper tissue levels; i.e. at the muscle. The visual comparison is supported by numerical analysis in table 2.

The pressure inside the soft tissue of the sacral area under the dressing was analysed and compared between model I and II in terms of volume of soft tissue subject to higher pressure. The results are summarized in table 2 below.

TABLE 2

| Model I (volume mm3) | Model II (volume mm3) | Pressure normalized |
| --- | --- | --- |
| 277 | 116 | Higher than 50% of max pressure |
| 1626 | 209 | Between 40% and 50% of max pressure |

Table 2 shows that the volume of soft tissue subject to high pressure is significantly lower when a dressing according to the invention is used.

Figure 8A:
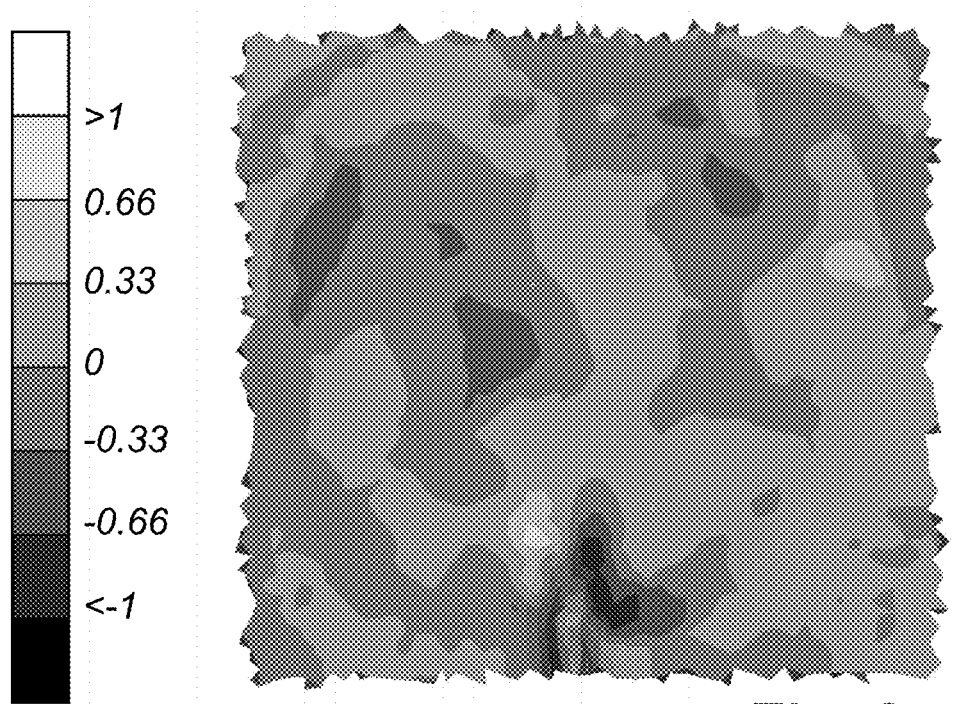
FIG. 8 illustrates images obtained from FE modelling of the sacrum region and the effect of shear forces on the tissue when the dressing of the invention has been applied (FIG. 8a) compared to a dressing having a low stiffness in the longitudinal (y) direction (FIG. 8b).
Figure 8B:
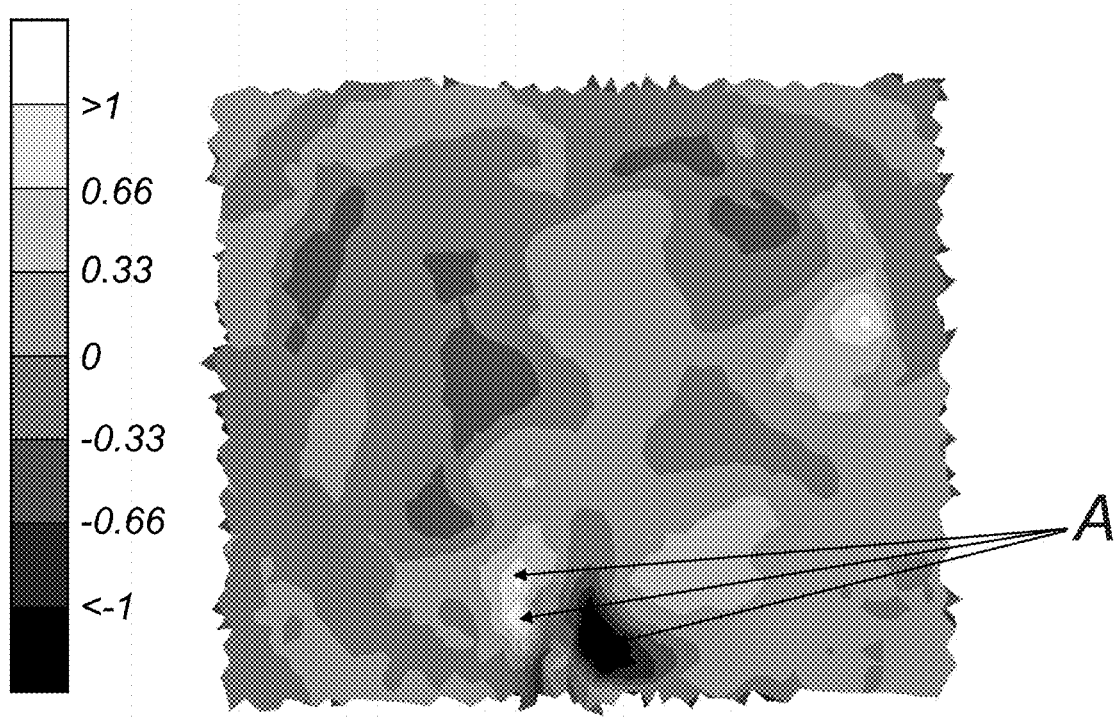

Furthermore, a comparison with respect to the distribution of shear stresses in the soft tissue under the sacrum area was made between model II and model III. The scale for the normalized stresses goes from Oto>1 and Oto<−1, depending on the direction of the shear stresses. FIG. 8 illustrates the effect of shear forces on the tissue when the dressing of the invention is used (FIG. 8a), compared to a dressing having a low tensile strength in the longitudinal (y) direction; i.e. model III (FIG. 8b). As can be seen in FIG. 8b, the lower part of the sacrum area presents stresses higher in absolute value to 1 (see arrows labeled A). Such extreme values are not present with the inventive dressing (FIG. 8a). A more even distribution of shear stresses is observed with the inventive dressing, in opposition to isolated shear stress areas. Pressure ulcers often occur at the coccyx, where the soft tissue is very thin. A more controlled shear stress distribution in this area provides an improved environment at the skin.

Comparative FE Studies

Figure 9:
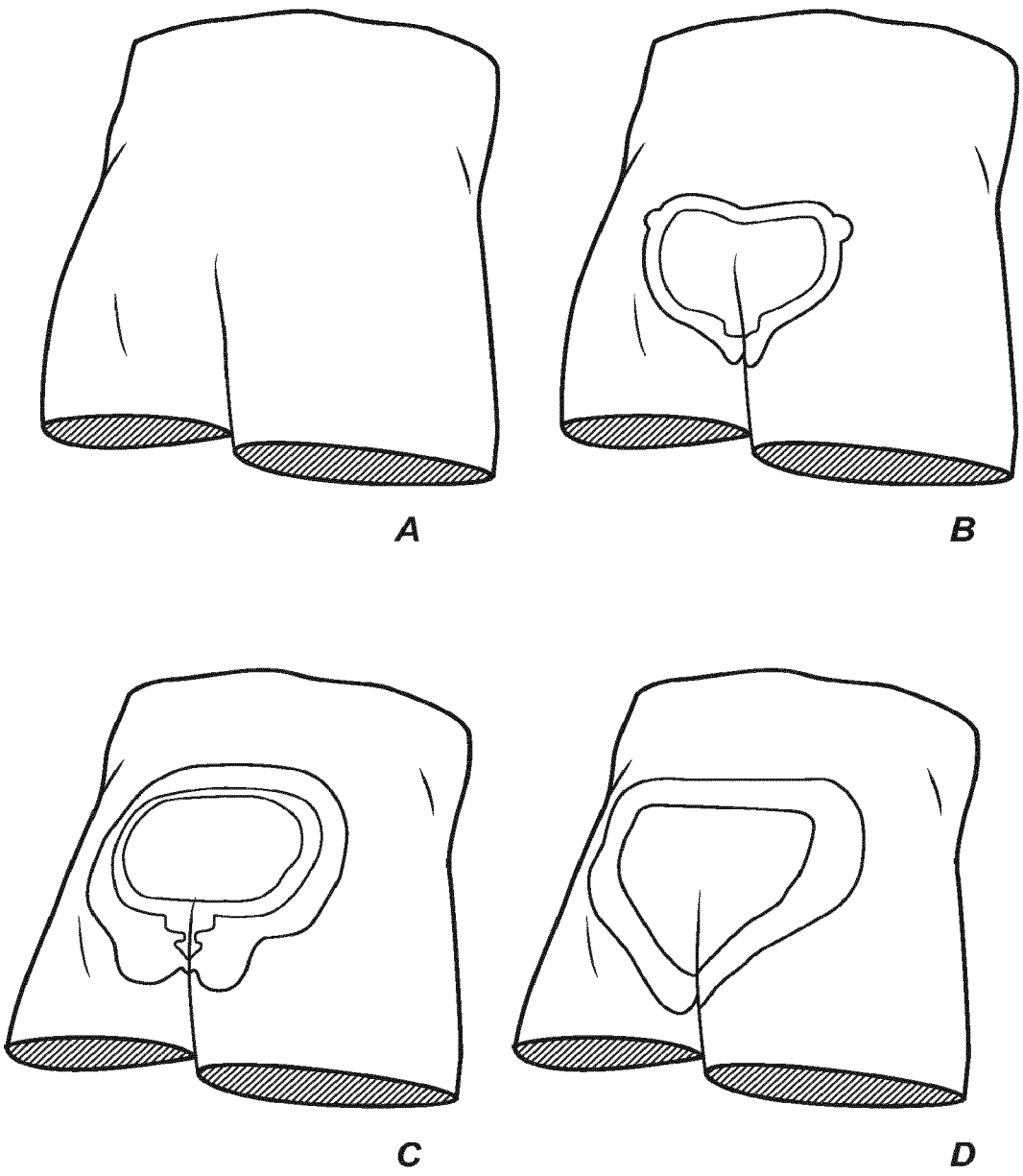
FIG. 9 illustrates FE models of the pelvis used for studying the distribution of stresses without dressing (A), with the dressing of the invention (B) and with two comparative dressings (C and D).

The inventive dressing, hereinafter referred to as reference sample B (corresponding to reference sample A in table 1) was compared with reference to samples C (Allevyn® Life Sacrum) and D (Aquacel foam Sacrum), as well as no dressing (A) (see FIG. 9). The effect on tissue compression was studied as above. In addition, the effect of additional shear forces on the skin, fat and at the muscle was also analysed. This was to illustrate the effect on the skin cells and deeper tissue (fat and muscle) cells in a healthcare setting where the head of the bed is elevated, creating a sliding of the body. The sliding will increase the deformation of the soft tissue and the shear stresses (see FIGS. 2c and d). The sliding was simulated by adding displacement of the body towards the fix mattress, and the increase of the shear stresses in the soft tissues was measured.

The material properties of the different dressings were defined by actual laboratory measurements in tension and compression based on ASTM D 882 and ASTM D 3574. The effect of compression and sliding of the pelvis was analysed in both dry and in wet conditions (to simulate sweating and a wear time of at least 24 hours). Wet material properties of the dressings were obtained by adding water to the adhesive surface before the tests were conducted. Droplets of water were placed evenly over the test surface area (0.04 ml/cm2) and allowed to absorb for 10 minutes before the test.

In order to get a deeper understanding of the distribution of the stresses, a comparison was made of the effect without dressing (FIG. 9a) and with dressings B, C and D, in both dry and wet conditions, and studying both the effect when subject to pure compression (horizontal position of the patient), and to compression and shear forces (elevated position of the patient).

The effect of the different dressings was studied in terms of mean pressure, von Mises stresses, transverse and shear stresses in the plane.

The critical value of stresses correspond to about 1 kg for 10 cm2 (around 10 kPa), except for the shear stresses in pure compression, where a lower value of the critical stresses was used, corresponding to about 100 g for 10 cm2 (around 1 kPa), as the stresses are applied parallel to the muscle fibers and therefore against a more natural compressive behaviour.

In pure compression (horizontal position), relevant stresses were investigated at several soft tissue levels to understand the effect of gravity on the soft tissue when the patient is in horizontal position with and without the dressings. The following was studied:

The mean pressure at the surface of the skin
The von Mises stresses at the fat
The von Mises stresses at the muscle
The shear stresses at the muscle next to the bones, at the interface with the sacrum (anterior part) to show the effect of shear stresses at the muscles due to the asperities of the bones To understand the effect of sliding and shear on the soft tissue when the patient is in elevated position, shear forces were added, and the following was studied:

The transverse stress in lateral direction (in the plane) at the surface of the skin
The shear stresses at the fat
The shear stresses at the muscle
The shear stresses at the muscle next to the bones, at the interface with the sacrum (anterior part).

One way to evaluate the performance of the dressings is to define its ability to reduce the volume of tissue under critical stresses. The performance of the dressing can therefore be defined as the percentage reduction of volume of tissue under critical stress when compared to no dressing:

$$\text{Reduction (\%)} = \frac{(V_{nd} - V_d)}{V_{nd} \times 100}$$

with Reduction (%)=percentage reduction of volume of tissue under critical stress
with Vnd=Volume of tissue under critical stress with no dressing
with Vd=Volume of tissue under critical stress with dressing To illustrate the concept of percentage reduction of volume of tissue under critical stress, the following ranking was used:

Reduction 100%=GOOD, with the dressing no tissue is under critical stress.
Reduction 50%=FAIR, half of the volume of tissue is under critical stress with the dressing compared to without.
Reduction 0%=BAD, there is no improvement with the dressing compared to without in terms of stress levels in the tissue.

In order to account for the approximation of FE analysis and for the validated subject specific anatomical model used, ranges with a 10% step were presented instead of specific values.

The following table presents the percentage reduction of volumes of tissue under critical stresses for the different soft tissue layers, skin, fat, muscle and muscle at the bones. The calculation defined the percentage of reduction of volume of tissue under critical stress with dressings on in both dry and wet conditions compared to the volume of tissue under critical stress without dressing. Relevant stresses in pure compression, simulating horizontal position (tables 3 and 5), and in compression plus shear stresses, simulating an elevated position (tables 4 and 6) were measured.

TABLE 3

Reduction of volume of tissue (%) under critical stress in dry condition (horizontal position)

| Reference dressing | Skin | Fat | Muscle | Muscle at bones |
|---|---|---|---|---|
| B | 90-100% | 80-90% | 90-100% | 50-60% |
| C | 0-10% | 0-10% | 0-10% | 0-10% |
| D | 90-100% | 20-30% | 10-20% | 0-10% |

TABLE 4

Reduction of volume of tissue (%) under critical stress in dry condition (elevated position)

| Reference dressing | Skin | Fat | Muscle | Muscle at bones |
|---|---|---|---|---|
| B | 90-100% | 90-100% | 80-90% | 80-90% |
| C | 0-10% | 0-10% | 0-10% | 0-10% |
| D | 0-10% | 0-10% | 0-10% | 0-10% |

TABLE 5

Reduction of volume of tissue (%) under critical stress in wet condition (horizontal position)

| Reference dressing | Skin | Fat | Muscle | Muscle at bones |
|---|---|---|---|---|
| B | 90-100% | 60-70% | 90-100% | 50-60% |
| C | 0-10% | 0-10% | 0-10% | 0-10% |
| D | 90-100% | 30-40% | 90-100% | 0-10% |

TABLE 6

Reduction of volume of tissue (%) under critical stress in wet condition (elevated position)

| Reference dressing | Skin | Fat | Muscle | Muscle at bones |
|---|---|---|---|---|
| B | 90-100% | 90-100% | 90-100% | 90-100% |
| C | 0-10% | 0-10% | 0-10% | 0-10% |
| D | 0-10% | 0-10% | 0-10% | 0-10% |

FIG. 10 illustrates the stresses in the soft tissue under the dressing area in a simulated elevated position, in wet conditions. Critical stresses are represented in white, and the scales have been normalized.

Figure 10A:
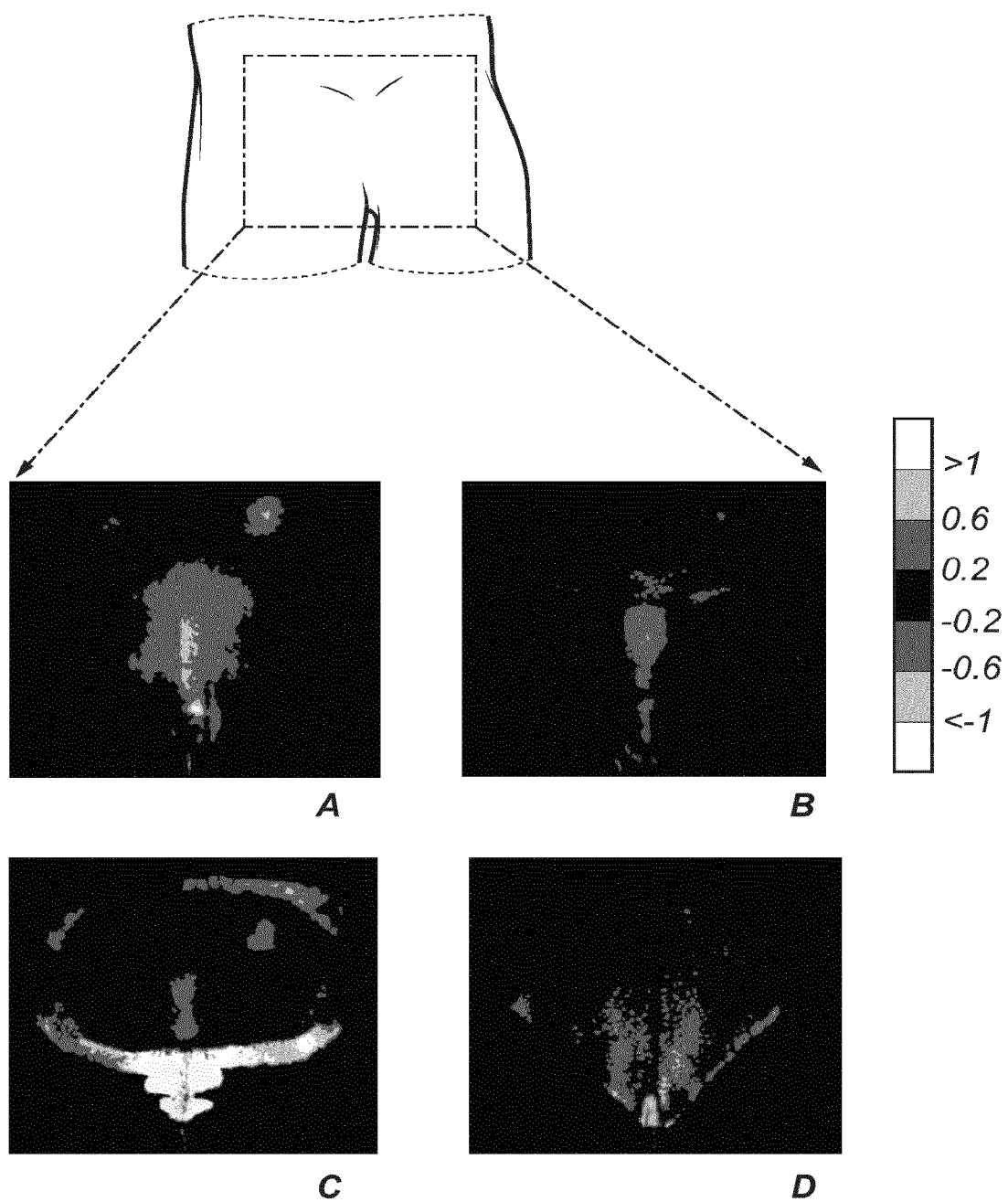
FIG. 10a illustrates the distribution of stresses at the skin under the dressing of the invention compared to no dressing and two comparative dressings in wet condition, elevated bed position.
Figure 10B:
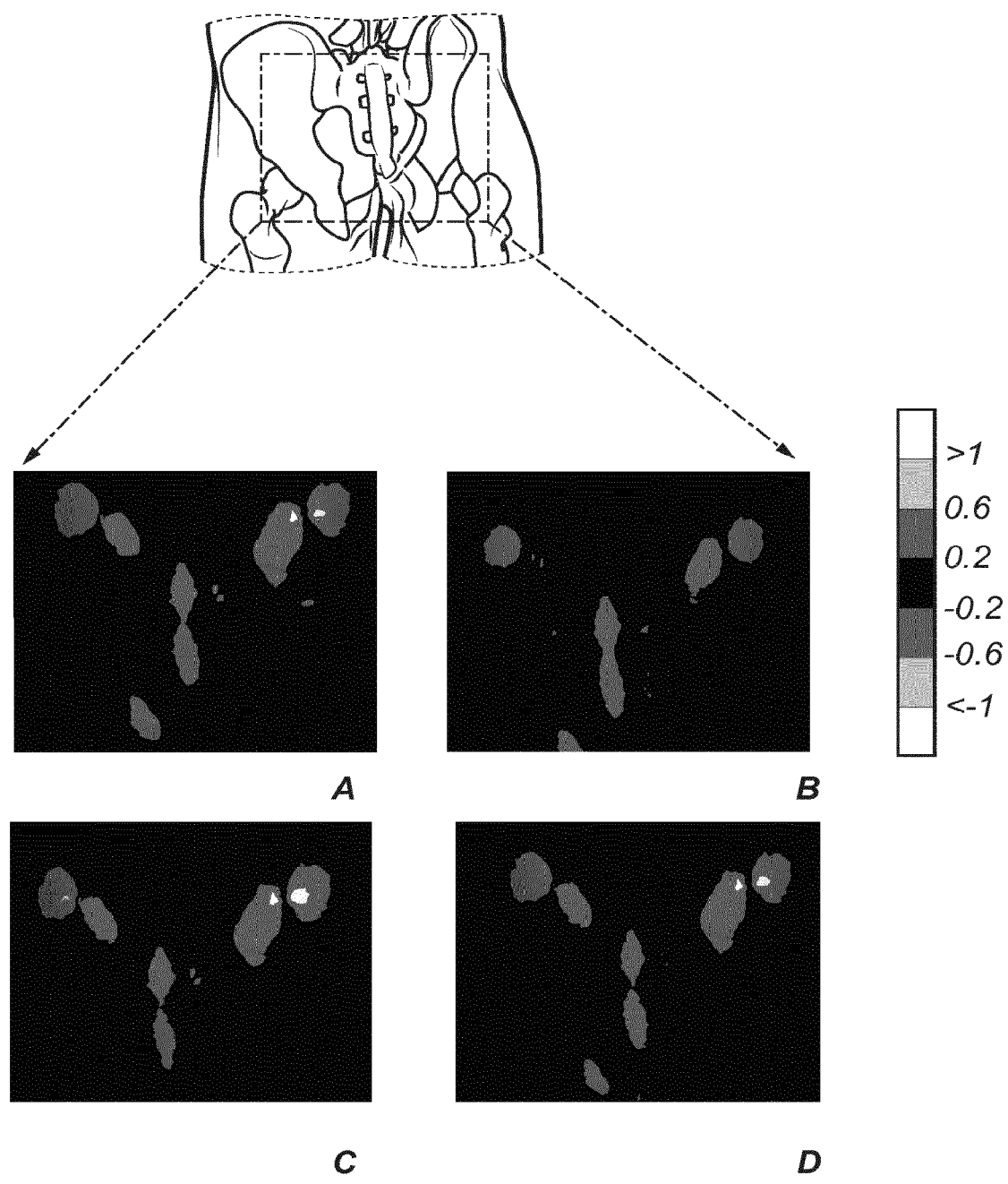
FIG. 10b illustrates the distribution of stresses at the muscle at the sacrum area of the invention compared to no dressing and two comparative dressings in wet condition, elevated bed position.

FIG. 10a illustrates the transverse stresses at the skin under the dressing area in a simulated elevated position, in wet conditions. FIG. 10b illustrates the shear stresses at the muscle at the sacrum area in elevated position, wet conditions.

It can be concluded that the dressing of the invention successfully reduces the pressure and stresses inside the soft tissue, both when the patient is in a horizontal, and elevated position (FIG. 10). The comparative dressings do not perform as well, especially in the case of shear induced by elevated position.

The inventive dressing spreads the stresses on the entire pad to avoid pressure peaks at the skin level. It also prevents critical stresses inside the soft tissue, especially limiting stresses originating from the bony prominences and spreading in the soft tissue until the skin.

Other embodiments of the invention will be apparent to those skilled in the art from consideration of the specification or practice of the invention disclosed herein. It is intended that the specification and examples be considered as exemplary only, with the true scope of the invention being indicated by the following claims.

The invention claimed is:

1. A medical dressing for application to a contoured surface of a human body, the dressing having a central portion and a surrounding border portion, the dressing further comprising:
   a backing layer;
   a body contact layer comprising a film covered by a silicone adhesive layer, the body contact layer being coextensive with the backing layer;
   a pad positioned between the backing layer and the body contact layer, the pad further comprising:
      a first layer,
      a second layer, and
      a third layer,
   wherein the first layer has a higher affinity for liquid than the second layer of the pad,
   wherein the first layer is positioned between the backing layer and the second layer,
   wherein the second layer is positioned between the third layer and the first layer,
   wherein the third layer is positioned between the second layer and the body contact layer,
   wherein the backing layer and the body contact layer extend beyond a periphery of the pad to define the border portion of the dressing along the periphery of the pad extending along a contour of the pad,
   wherein the body contact layer further comprises a plurality of perforations extending through the body contact layer for aiding in absorption of a liquid into the pad,
   wherein the plurality of perforations extends through the film and the silicone adhesive layer of the body contact layer,
   wherein the pad has a lower region having a narrower width than an upper region of the pad such that the pad tapers towards the lower region, the pad further being symmetric about a longitudinal center line and comprises a first lobed portion on one side of the longitudinal center line and a second lobed portion on the other side of the longitudinal center line, and
   wherein the central portion has a tensile strength at 25% elongation in a longitudinal (y) direction that is higher than the tensile strength at 25% elongation in a lateral (x) direction, such that the central portion is stiffer in the longitudinal (y) direction and is more stretchable in the lateral (x) direction, such that the dressing is configured to absorb and redistribute pressure forces over a larger area for reducing a magnitude of the force applied to the skin of the body.

2. The medical dressing according to claim 1, wherein the first layer comprises a superabsorbent polymer including at least one of superabsorbent fibers or superabsorbent particles.

3. The medical dressing according to claim 2, wherein the second layer comprises a nonwoven material.

4. The medical dressing according to claim 3, wherein the third layer comprises a foam material.

5. The medical dressing according to claim 1, wherein the central portion has a dry tensile strength in the longitudinal (y) direction of at least 60 N per 50 mm at an elongation of 25%, as measured by the test method ASTM D 882-12.

6. The medical dressing according to claim 5, wherein the central portion has a dry tensile strength in the longitudinal (y) direction of at least 70 N per 50 mm at an elongation of 25%, as measured by the test method ASTM D 882-12.

7. The medical dressing according to claim 1, wherein a nonwoven material of the second layer comprises a fibrous web having a homogenous arrangement of fibers generally aligned along the longitudinal (y) direction of the dressing for increasing the tensile strength of the central portion in the longitudinal (y) direction.

8. The medical dressing according to claim 1, wherein the backing layer has a friction coefficient of less than 1.5, as measured by the test method ASTM D 1894-14.

9. The medical dressing as claimed in claim 1, wherein a first and a second lobed portions form part of lobed upper sides of a heart shape, wherein the first and second lobed portions are separated by a forked portion at a lower region of the heart shape.

10. The medical dressing according to claim 1, wherein the border portion has a tensile strength of between 3.5 and 10 N per 50 mm at an elongation of 25%, as measured by ASTM D 882-12.

11. The medical dressing according to claim 1, wherein the central portion has a tensile strength at 25% elongation in the longitudinal (y) direction that is at least 2.5 times higher than the tensile strength at 25% elongation in the lateral (x) direction.

12. The medical dressing according to claim 1, wherein the pad is divided by a lateral center line into an upper pad region with an upper lateral edge, and a lower pad region with a lower lateral edge, wherein the width, x1, of the lower lateral edge of the pad is between 10 and 40% of the maximum width, x2, of the pad in the lateral (x) direction.

13. The medical dressing according to claim 1, wherein the plurality of perforations includes a set of perforations extending through a portion of the body contact layer that defines the border portion.

14. A medical dressing for application to a contoured surface of a human body, the dressing having a central portion and a surrounding border portion, the dressing further comprising:
a backing layer;
a body contact layer comprising a film covered by a silicone adhesive layer, the body contact layer being coextensive with the backing layer;
a pad positioned between the backing layer and the body contact layer, the pad further comprising:
a first layer,
a second layer, and
a third layer;
wherein the first layer has a higher affinity for liquid than the second layer of the pad,
wherein the first layer is positioned between the backing layer and the second layer,
wherein the second layer is positioned between the third layer and the first layer,
wherein the third layer is positioned between the second layer and the body contact layer,
wherein the backing layer and the body contact layer extend beyond a periphery of the pad to define the border portion of the dressing along the periphery of the pad extending along a contour of the pad,
wherein the body contact layer further comprises a plurality of perforations extending through the body contact layer for aiding in absorption of a liquid into the pad,
wherein the plurality of perforations extends through the film and the silicone adhesive layer of the body contact layer,
wherein the central portion has a dry tensile strength in a longitudinal (y) direction of at least 60 N per 50 mm at an elongation of 25%, as measured by the test method ASTM D 882-12, and wherein the central portion has a tensile strength at 25% elongation in a lateral (x) direction that is less than the tensile strength at 25% elongation in the longitudinal (y) direction, such that the central portion is stiffer in the longitudinal (y) direction and is more stretchable in the lateral (x) direction, such that the dressing is configured to absorb and redistribute pressure forces over a larger area for reducing a magnitude of the force applied to the skin of the body.

15. The medical dressing according to claim 14, wherein the first layer comprises a superabsorbent polymer including at least one of superabsorbent fibers or superabsorbent particles.

16. The medical dressing according to claim 15, wherein the second layer comprises a nonwoven material.

17. The medical dressing according to claim 16, wherein the third layer comprises a foam material.

18. The medical dressing according to claim 17, wherein the foam material comprises a polyurethane foam, and wherein the nonwoven material comprises viscose and polyethylene.

19. The medical dressing according to claim 14, wherein a nonwoven material of the second layer comprises a fibrous web having a homogenous arrangement of fibers generally aligned along the longitudinal (y) direction of the dressing for increasing the tensile strength of the central portion in the longitudinal (y) direction.

20. The medical dressing according to claim 14, wherein the border portion has a tensile strength of between 3.5 and 10 N per 50 mm, at an elongation of 25%, as measured by ASTM D 882-12.

21. The medical dressing according to claim 14, wherein the central portion has a tensile strength at 25% elongation in the longitudinal (y) direction that is at least 2.5 times higher than the tensile strength at 25% elongation in the lateral (x) direction.

* * * * *